United States Patent [19]

DeYoung et al.

[11] Patent Number: 6,074,617
[45] Date of Patent: Jun. 13, 2000

[54] STAT SHUTTLE ADAPTER AND TRANSPORT DEVICE

[75] Inventors: Thomas DeYoung, Stormville, N.Y.; Adam Perlman, Ridgewood, N.J.

[73] Assignee: Bayer Corporation, Tarrytown, N.Y.

[21] Appl. No.: 09/113,640

[22] Filed: Jul. 10, 1998

[51] Int. Cl.⁷ .................................................. G01N 35/02
[52] U.S. Cl. .......................... 422/104; 422/63; 422/65; 436/43; 436/47
[58] Field of Search ............................. 422/63, 65, 102, 422/103, 104; 436/43, 47, 48

[56] References Cited

U.S. PATENT DOCUMENTS

| | | | |
|---|---|---|---|
| 3,897,216 | 7/1975 | Jones | 422/65 |
| 4,066,412 | 1/1978 | Johnson et al. | |
| 4,236,825 | 12/1980 | Gilford et al. | 356/414 |
| 4,238,450 | 12/1980 | Bredeweg et al. | |
| 4,534,465 | 8/1985 | Rothermel et al. | 206/443 |
| 5,350,564 | 9/1994 | Mazza et al. | 422/63 |
| 5,374,395 | 12/1994 | Robinson et al. | |
| 5,623,415 | 4/1997 | O'Bryan et al. | 364/478.13 |
| 5,650,125 | 7/1997 | Bosanquet | 422/102 |
| 5,651,941 | 7/1997 | Stark et al. | 422/104 |
| 5,700,429 | 12/1997 | Buhler et al. | 422/104 |
| 5,735,387 | 4/1998 | Polaniec et al. | 198/690.1 |
| 5,762,878 | 6/1998 | Clark et al. | |
| 5,769,775 | 6/1998 | Quinlan et al. | |
| 5,788,928 | 8/1998 | Carey et al. | 422/102 |
| 5,897,835 | 4/1999 | Seaton et al. | 422/104 |
| 5,952,218 | 9/1999 | Lee et al. | 435/288.7 |
| 5,959,221 | 9/1999 | Boyd et al. | 72/864.24 |

*Primary Examiner*—Long V. Le
*Attorney, Agent, or Firm*—Andrew L. Klawitter, Esq.; Rodman & Rodman

[57] ABSTRACT

The stat shuttle adapter and transport device includes a conveyor with a movable platform for securement of the stat shuttle adapter. The stat shuttle adapter is a universal holding device that includes a carrier housing having male and female surfaces that engage complementary shaped female or male surfaces of a rack that is held by the carrier housing. The conveyor has a forward load position wherein racks are loaded onto the carrier housing. The conveyor also has a rearward unload position wherein the loaded rack is locked onto the carrier housing to facilitate removal of the contents of the rack from the carrier housing without upsetting the rack. A latch device on the carrier housing is normally biased to a lock position but is maintained in an unlock position when the carrier housing is at the forward load position of the conveyor. A latch engagement device on the conveyor maintains the latch in the unlock position while the carrier housing is at the forward load position of the conveyor. Once the conveyor moves the carrier housing away from the forward load position toward the rearward unload position the latch device is free to move to the normal lock position wherein the loaded rack is locked to the carrier housing. As the conveyor moves the carrier housing toward to the rearward unload position the latch device remains in the lock position.

11 Claims, 26 Drawing Sheets

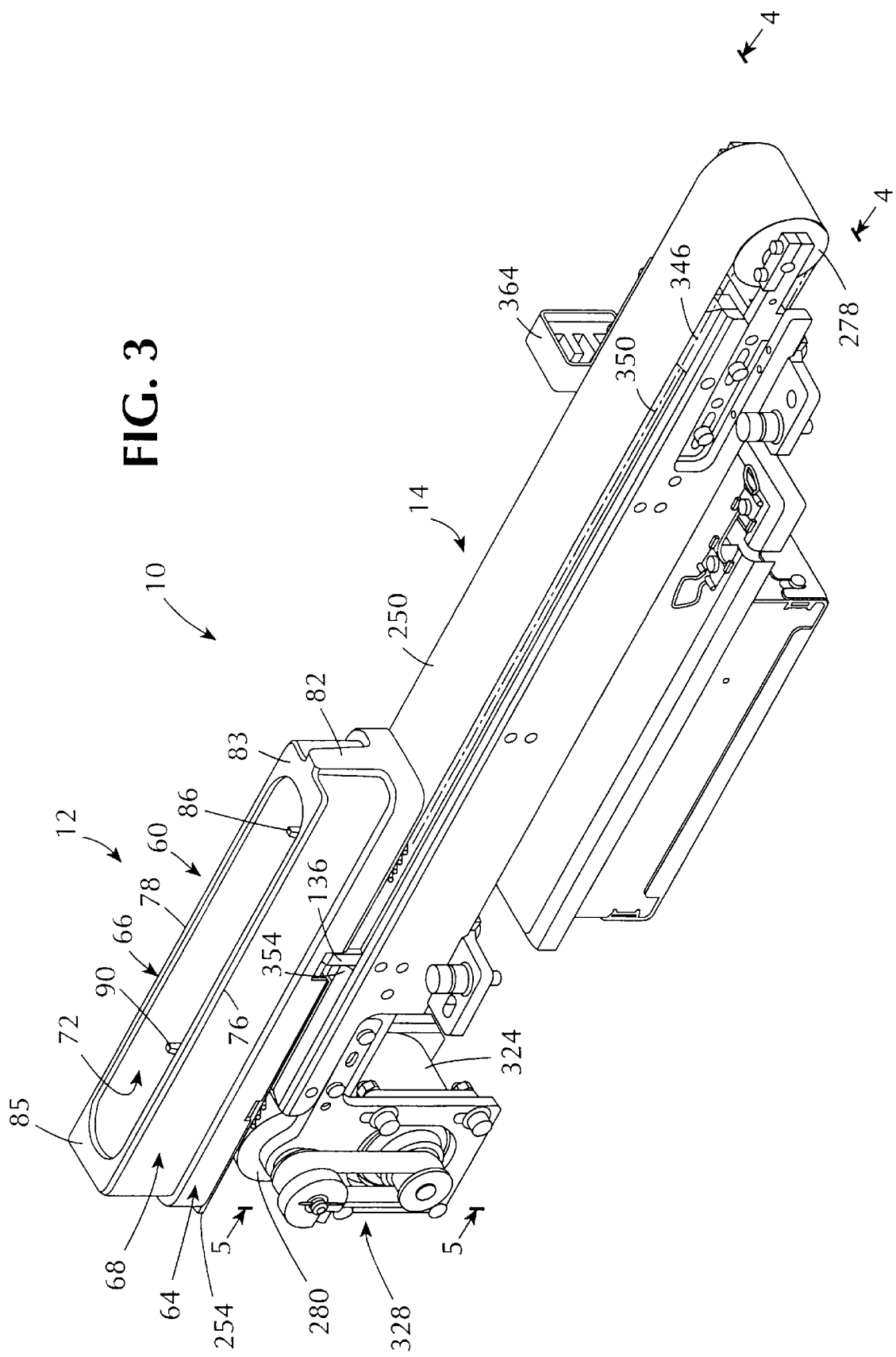

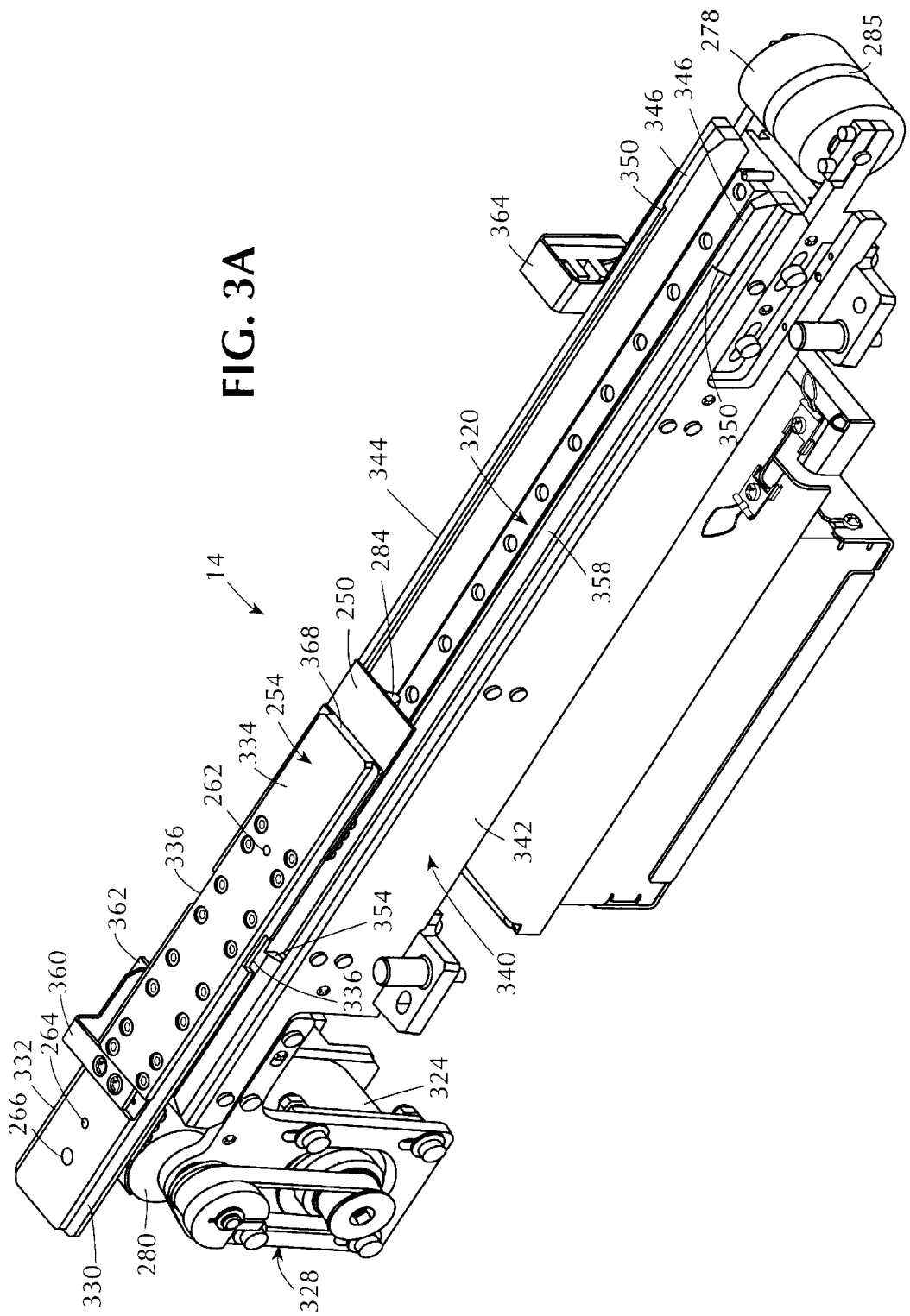

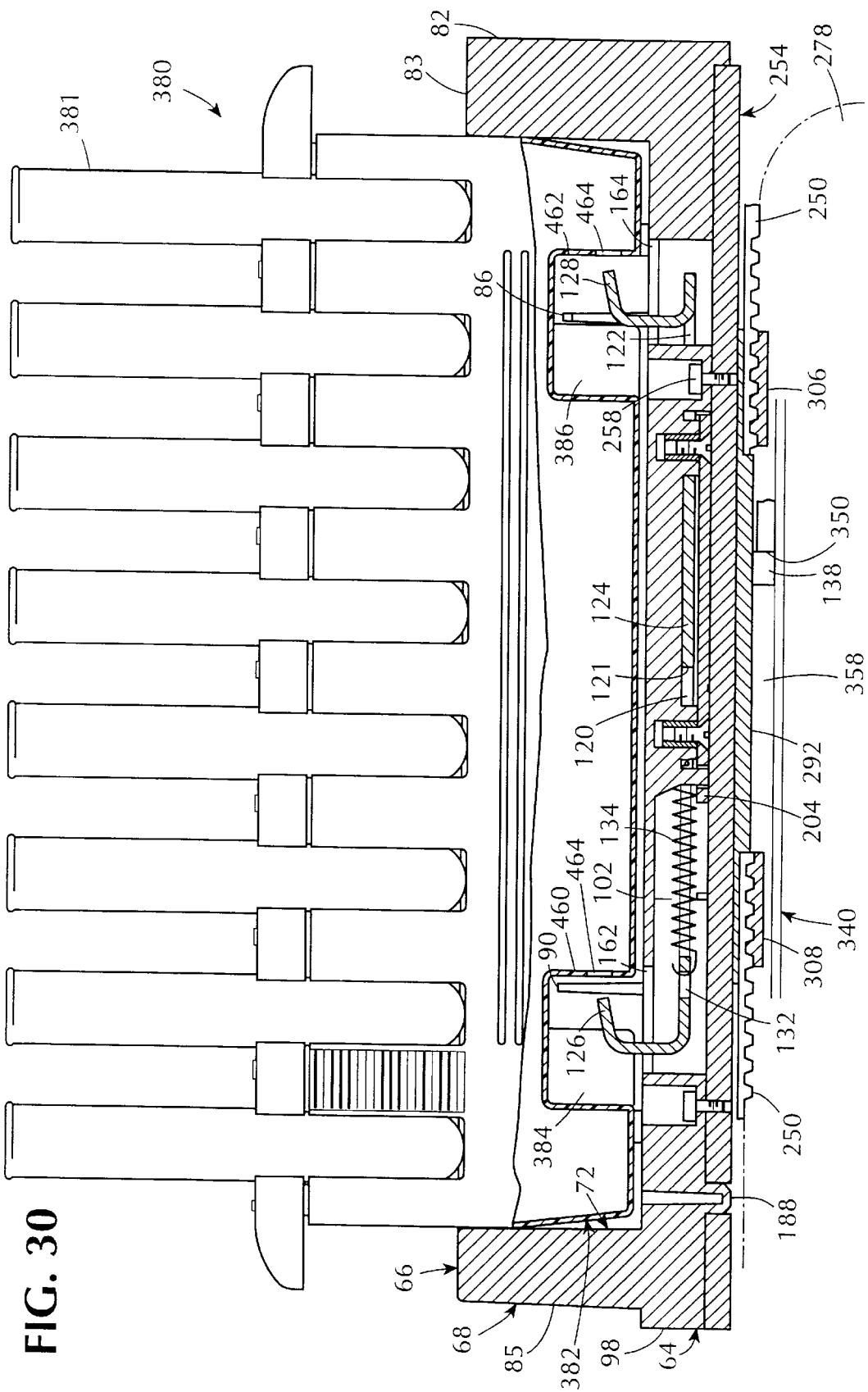

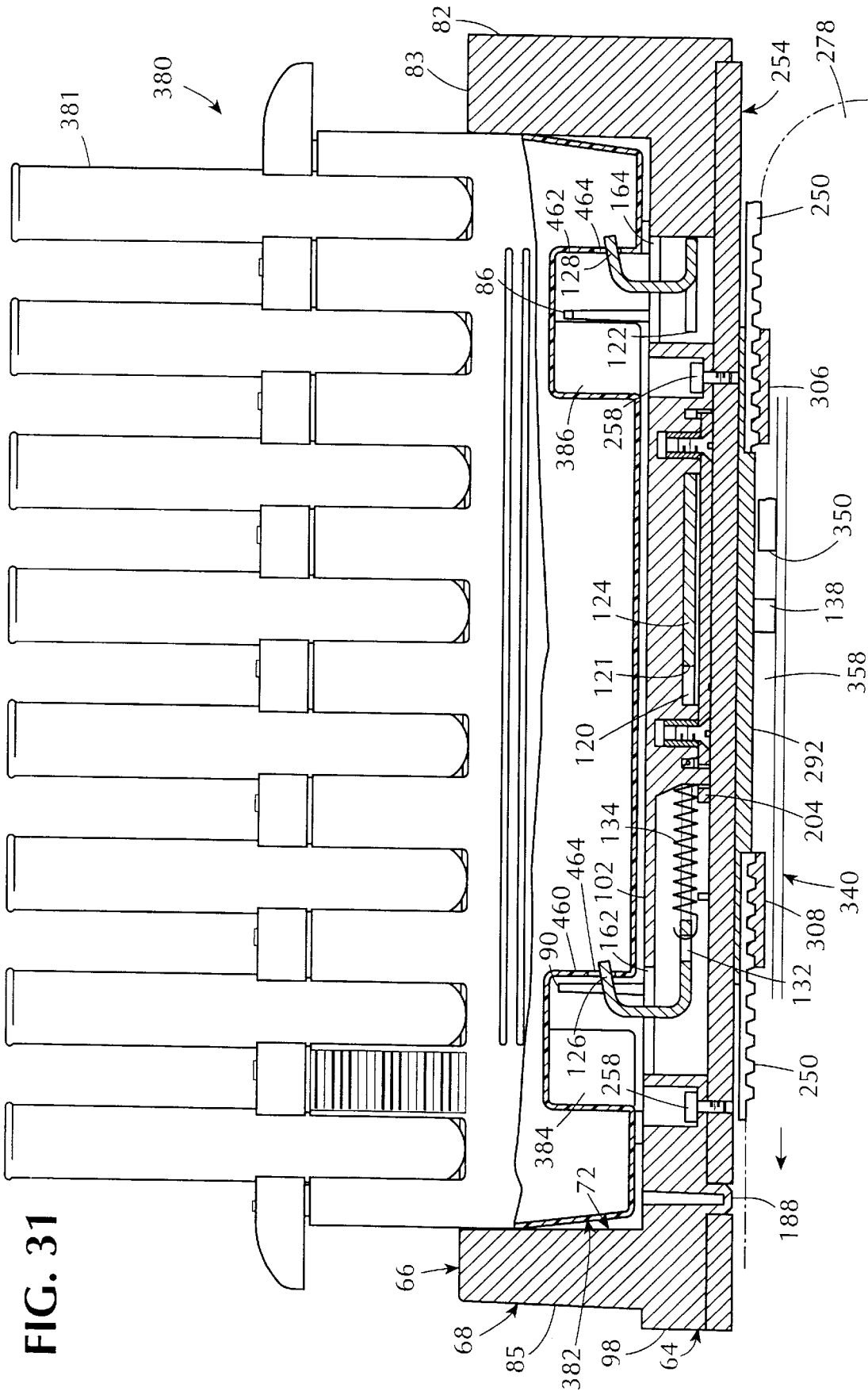

STAT SHUTTLE ADAPTER AND TRANSPORT DEVICE

BACKGROUND OF THE INVENTION

This invention relates to transport devices for automatic sampling systems and more particularly to a stat shuttle adapter and transport device for immediate automated delivery of sample, reagent or diluent to a sample analysis system.

Automatic testing of body fluids such as blood samples is usually carried out in a predetermined sequence of operations performed in a sample analysis system. An automatic sample analysis system such as shown in U.S. Pat. Nos. 5,268,147 and 5,399,497 generally operates with a steady input of samples that can be delivered to the analysis system either manually or automatically. Ideally, the delivery of samples to the automatic sample analysis system is synchronized with the operational speed of the sample analysis system for optimum coordination of sample input, sample analysis and collection of completed test samples. Input samples are thus typically arranged in an input queue and are subject to a waiting time at the input queue before entering the sample analysis system.

In some instances it is necessary to obtain immediate entry of a sample or other sample analysis ingredient into the sample analysis system. Immediate entry of a sample etc. into the sample analysis system is usually accomplished by interrupting the normal input sequence of sample to the sample analysis system in order to preempt the normal queue of input samples awaiting entry to the sample analysis system. A preemption process often requires a holding back of the input queue of samples to permit preferential delivery of a selected sample or other immediately required sample analysis ingredient to the sample analysis system.

Generally, when an input queue of samples is awaiting entry to a sample analysis system, data pertaining to the identification and position of such samples is automatically accumulated in a computerized monitoring system. When the input queue of samples is to be preempted it is often necessary for an operator to manually interrupt the automatic delivery of sample to the sample analysis system and manually perform a correction procedure in the automatic monitoring operations of the input delivery system. Manual preemption of a normal automatic input delivery sequence of sample to the sample analysis system can distract an operator from other process areas that require attention. Manual preemption of a normal automatic input delivery sequence can also be time consuming because of the need to make manual adjustments to the input delivery system to enable it to accommodate the immediately required sample analysis ingredients.

It is thus desirable to provide a stat shuttle adapter and transport device for providing immediate automated delivery of sample, reagent or diluent to a sample analysis system without manually interfering with the normal queue of input samples awaiting entry to a sample analysis system.

OBJECTS AND SUMMARY OF THE INVENTION

Among the several objects of the invention may be noted the provision of a novel transport device for immediate automated delivery of sample, reagent or diluent to a sample analysis system, a novel stat shuttle adapter and transport device for a sample analysis system for automated delivery of analysis ingredients to the sample analysis system, a novel stat shuttle adapter which accommodates a sample tube rack, a reagent package rack or a diluent package rack in a stable upright position, a novel stat shuttle adapter which accommodates different racks for different sample analysis components, a novel stat shuttle adapter that accommodates different racks for sample, reagent, and diluent by disposition of such racks onto the stat shuttle adapter without the need to apply any force or make any adjustment between the respective rack and the stat shuttle adapter, a novel stat shuttle adapter and transport device which includes a latch device that has an unlock position to permit easy loading of different racks onto the stat shuttle adapter and a lock position to hold the racks onto the stat shuttle adapter when the contents of the racks are being automatically transported and unloaded, a novel stat shuttle adapter and transport device wherein the transport device includes immovable latch engagement surfaces for causing movement of a latch from a normal lock position to an unlock position, a novel stat shuttle adapter and transport device wherein a carrier housing for different rack types is secured to the transport device for movement with the transport device and a novel stat shuttle adapter that co-acts with latch engagement structure on the transport device to cause latch movement on the adapter to selected lock and unlock positions.

Other objects and features of the invention will be in part apparent, and in part pointed out hereinafter.

In accordance with the present invention, the stat shuttle adapter and transport device includes a carrier housing for holding a rack and a conveyor with a movable platform for transporting the carrier housing from a forward load position of the conveyor to a rearward unload position of the conveyor. The load position refers to a loading of a rack on the carrier housing whereas the unload position refers to removal of the rack contents from the rack while the rack remains locked to the carrier housing on the conveyor.

The stat shuttle adapter and transport device provides automatic preemptive delivery of selected sample analysis ingredients to a sample analysis system that supersedes normal operation of an automatic input queue delivery system of untested samples to the sample analysis system.

The carrier housing has a peripheral wall that defines an inside female surface and an outside male surface for engaging complementary shaped male or female surfaces of different racks that can be held by the carrier housing. A latch device provided on the carrier housing is normally biased to a lock position wherein the latch secures the rack to the carrier housing. The latch device is movable to an unlock position that permits force free installation of the rack in the carrier housing and force free removal of the rack from the carrier housing.

The stat shuttle adapter and transport device is incorporated in a sample handler module that delivers untested sample to a sample analysis system and collects the tested sample from the sample analysis system after testing has been completed. The stat shuttle adapter and transport device preempts the normal queue of untested samples awaiting delivery to the sample analysis system and provides immediate automated delivery of one or more priority untested samples, a supply of reagent or a supply of diluent to the sample analysis system while the normal queue of untested samples is temporarily arrested from further movement.

The latch device for holding the racks to the carrier housing is slideably mounted on the carrier housing for slideable movement in opposite directions relative to a base portion of the carrier housing from the lock position to the unlock position and vice versa. The latch device includes at least one latch engagement member that projects into a female space of the carrier housing that is defined by the peripheral wall of the carrier housing. The latch device includes an actuator member for effecting movement of the latch device from the lock position to the unlock position.

The shuttle adapter device, which includes the carrier housing, is secured to a moveable platform of the transport device conveyor for movement from a forward load position of the conveyor to a rearward unload position of the conveyor. The conveyor includes first and second immovable actuator engagement surfaces that cooperate with the latch to move the latch from the lock position to the unlock position, depending upon whether the carrier housing is at the forward load position or the rearward unload position.

Thus when the carrier housing is in the forward load position the actuator member of the latch device engages the first immovable engagement surface of the conveyor to hold the latch device in an unlock position thereby permitting force free disposition of a rack onto the carrier housing.

When the carrier housing is moved by the conveyor away from the forward load position in the direction of the rearward unload position the carrier housing latch device is biased to a normal lock position that locks the rack to the carrier housing. The latch device normally remains in the lock position during the excursion of the carrier housing to the rearward unload position of the conveyor. Thus, when the carrier housing is in the rearward unload position of the conveyor the rack remains locked to the carrier housing which facilitates unloading of the rack contents.

If the latch device is inadvertently held in the unlock position during movement of the carrier housing the rearward unload position of the conveyor then the actuator member of the latch device will engage the second immovable actuator engagement surface. Such engagement or interference between the second immovable actuator engagement surface and the actuator member of the latch device will cause the latch device to move to the lock position thereby ensuring that whenever the carrier housing is in the rearward unload position the rack device is locked to the carrier housing.

The carrier housing and any racks that are transported on the carrier housing are provided with complementary keying surfaces and keying recesses to ensure predetermined orientation of a rack in the carrier housing.

When preemptive operation of the shuttle adapter and transport device is no longer required such operation can be suspended and the normal automatic movement of the input queue of sample racks to the sample analysis system can be reactivated without the need to manipulate or otherwise rearrange the input queue of sample racks awaiting delivery to the sample analysis system.

The invention accordingly comprises the constructions hereinafter described, the scope of the invention being indicated in the claims.

DESCRIPTION OF THE DRAWINGS

In the accompanying drawings,

FIG. 3 is a simplified schematic side perspective view of the stat shuttle adapter and transport device with the stat shuttle adapter at a rearward unload position on the transport device;

FIG. 3A is a view similar to FIG. 3 with the conveyor belt removed from the transport device and the stat shuttle adapter removed from an attachment platform of the transport device;

FIG. 30 is a front elevational view of the stat shuttle adapter at the forward load position on the transport device and showing the stat shuttle adapter latch device in the unlock position with the sample tube rack mounted thereon;

FIG. 31 is a view corresponding to FIG. 30 with the stat shuttle adapter latch device in a lock position as the transport device moves the stat shuttle adapter away from the forward load position to the rearward unload position.

Corresponding reference characters indicate corresponding parts throughout the several views indicate corresponding parts throughout the several views of the drawings, except where otherwise indicated.

DETAILED DESCRIPTION OF THE INVENTION

Figure 3B:
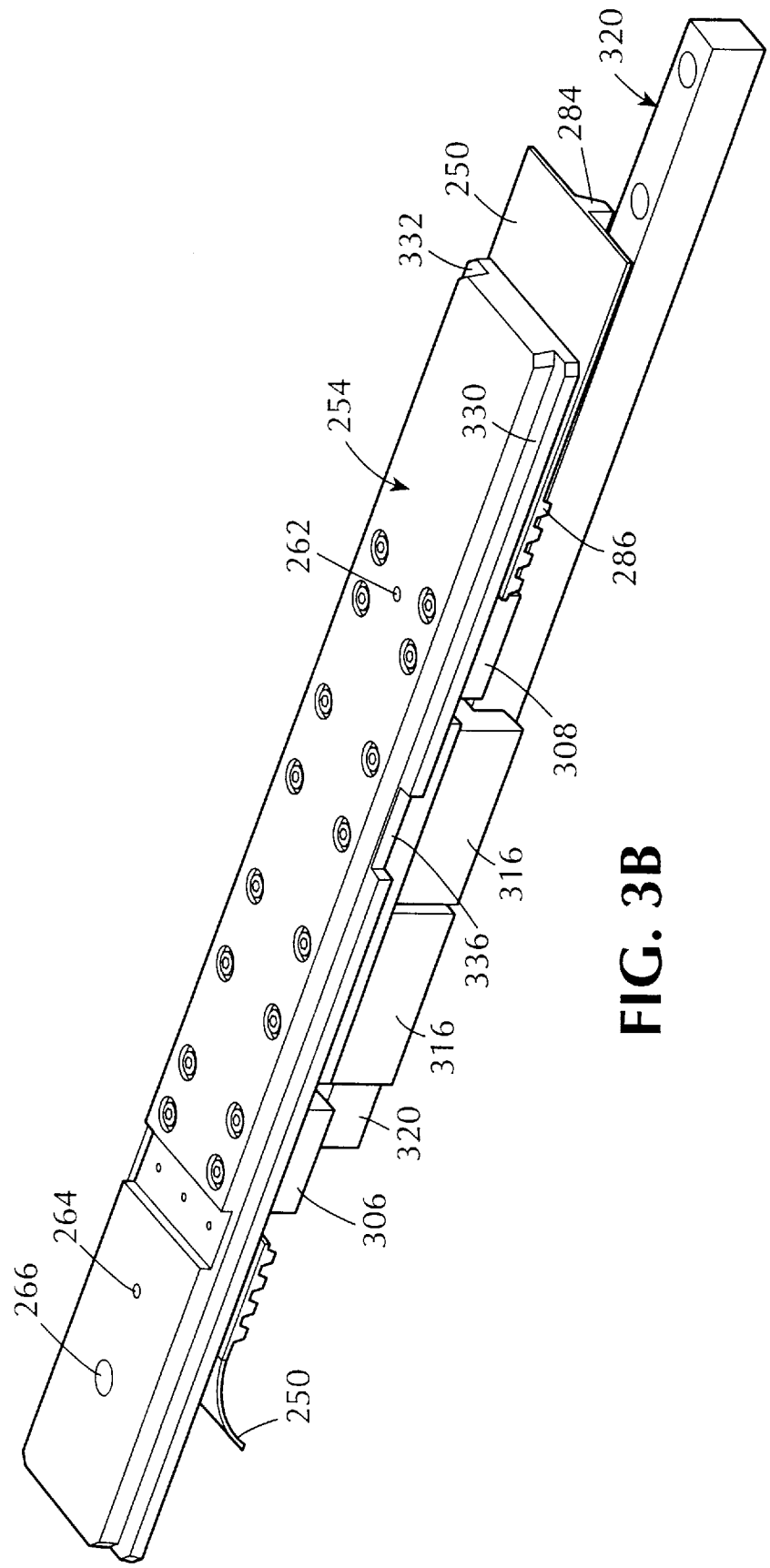
FIG. 3B is a top perspective fragmentary view thereof showing the attachment platform and underlying structure of the transport device.
Figure 3C:
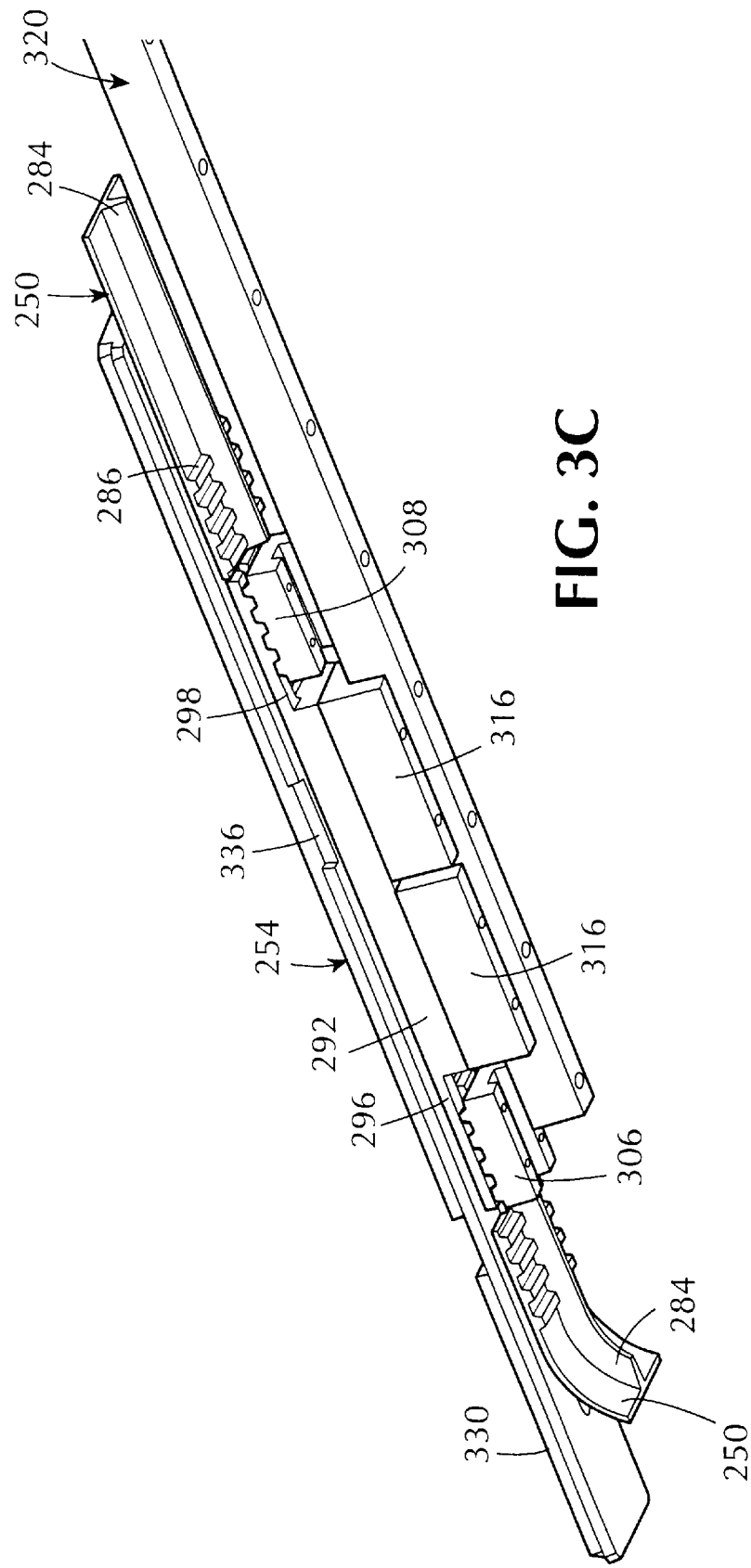
FIG. 3C is a bottom perspective fragmentary view of FIG. 3B.

Referring to the drawings a stat shuttle adapter and transport device incorporating one embodiment of the invention is generally indicated by the reference number 10 in FIG. 3.

The stat shuttle adapter and transport device 10 (hereinafter referred to as the stat shuttle 10) includes a stat shuttle adapter 12 (hereinafter referred to as the adapter 12) and a transport device 14.

Figure 1:
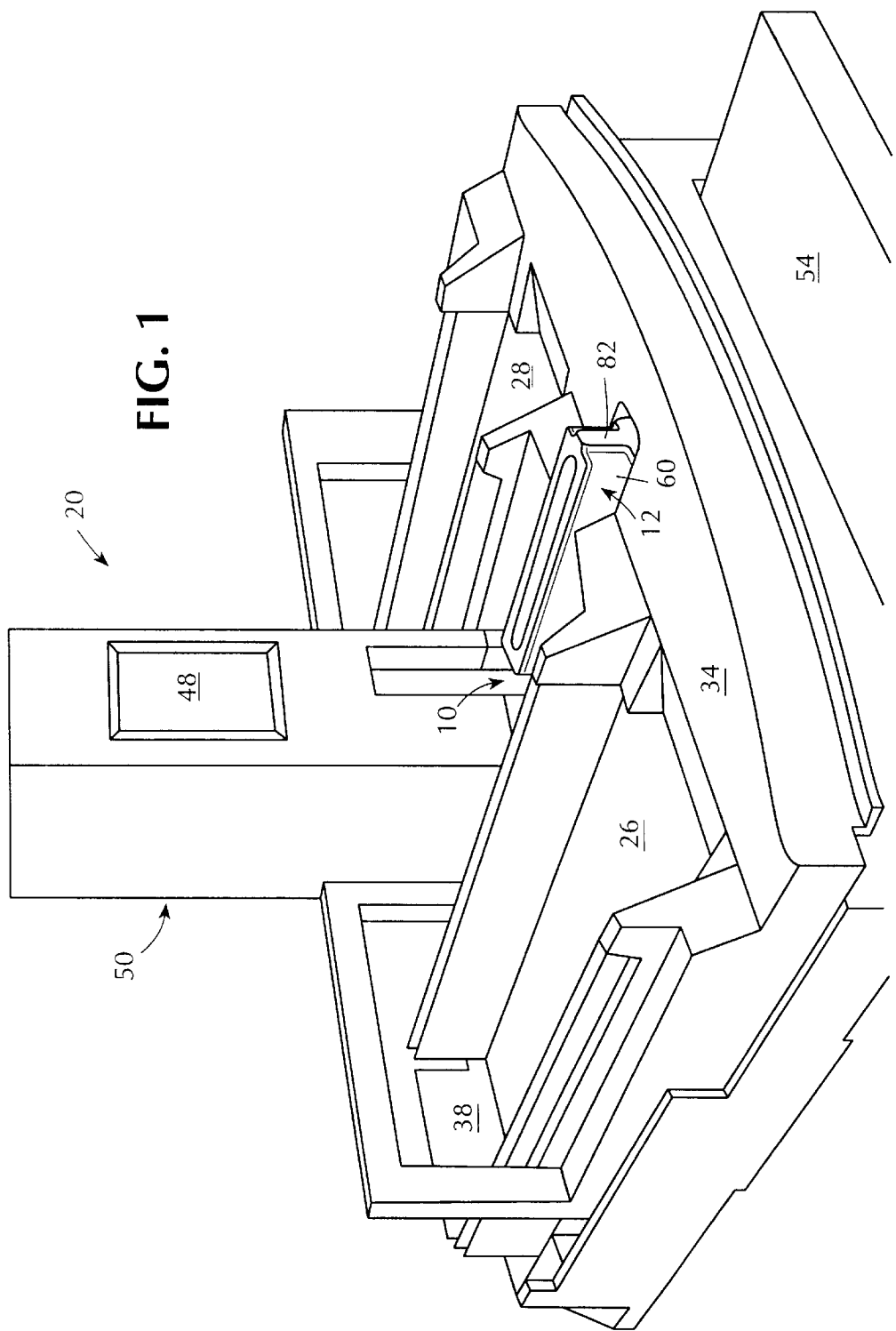
FIG. 1 is a simplified schematic side perspective view of a sample handler module incorporating one embodiment of the invention.

The stat shuttle 10 is a component of a sample handler module 20 shown in simplified schematic form in FIG. 1. The stat shuttle 10 is disposed between an input queue pathway 26 and an output queue pathway 28 of the sample handler module 20. More detailed operational features of the input and output queue pathways 26 and 28 of the sample handler module are disclosed in a co-pending application filed contemporaneously with this application.

Figure 2:
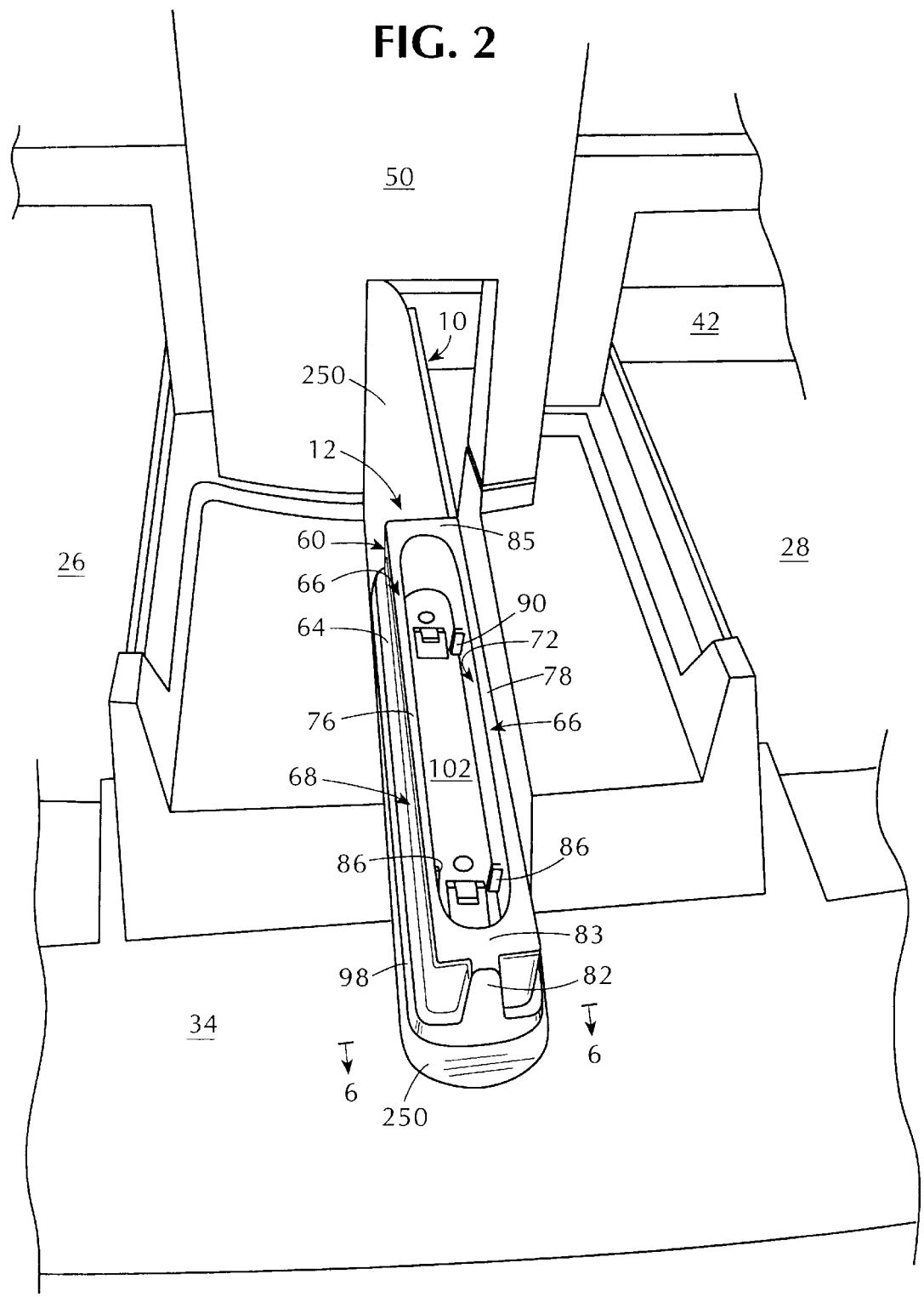
FIG. 2 is a simplified schematic fragmentary top perspective view thereof.
Figure 27:
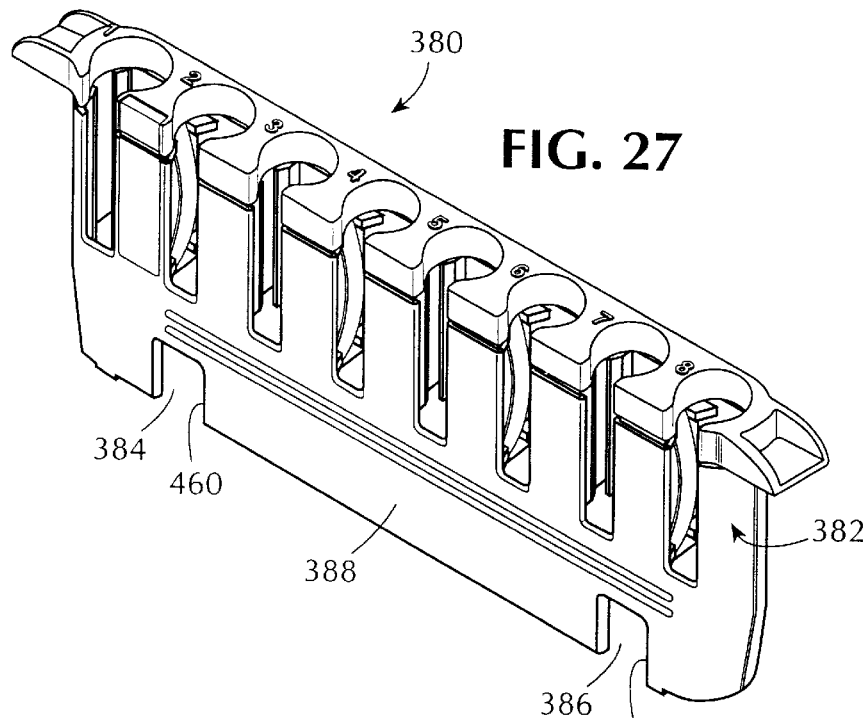
FIG. 27 is a simplified schematic perspective view of a sample tube rack.
Figure 28:
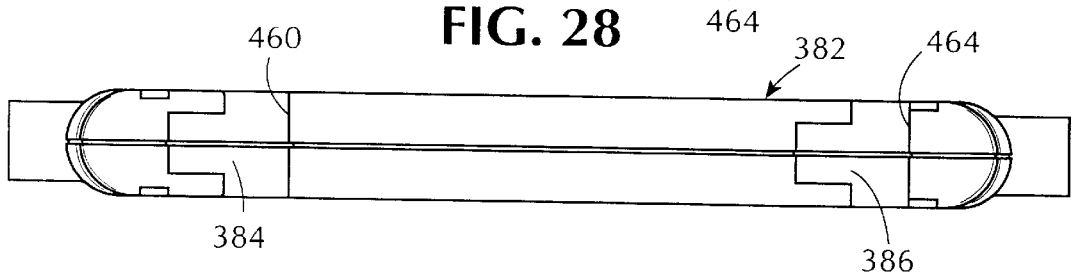
FIG. 28 is a bottom view thereof.
Figure 29:
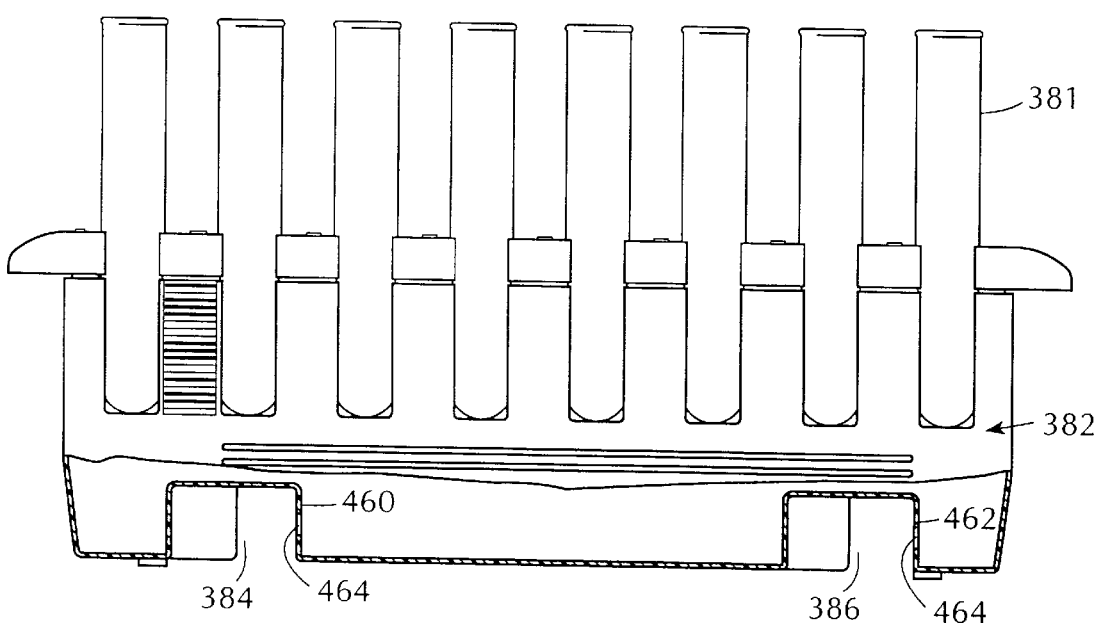
FIG. 29 is front elevational view thereof, partly shown in section.

During normal operation of the sample handler module 20, a plurality of sample tube racks 380 as shown in FIGS. 27–29 are placed at a front or forward end of the input queue 26 near a workstation area 34 of the sample handler module 20. The sample tube racks are moved from the forward end of the input queue pathway 26 at the workstation area 34 in a rearward direction to a cross feed transporter (not shown) at a rearward end 38 of the input queue pathway 26 for entry to a sample analysis system (not shown) of the type shown in U.S. Pat. No. 5,399,497. Once the samples in the racks 380 of FIGS. 27–29 are analyzed by the sample analysis system (not shown) they are placed in similar racks at a rearward end 42 (FIG. 2) of the output queue pathway 28 for movement from the rearward end 42 to a front or forward end of the output queue pathway 28 for collection or off-loading at the workstation area 34.

The movement of sample tube racks on the input and output queue pathways 26, 28 and the off-loading of the sample racks 380 from the input queue pathway 26 to a cross feed transport system (not shown) as well as the on-loading of the racks 380 from the sample analysis system (not shown) to the output queue pathway 28 is disclosed in more detail in the previously mentioned co-pending application filed on the same date as this application.

Thus in the usual course of operation of the sample handler module 20, untested samples are delivered to a sample analysis system in a queue of racks that proceed along the input queue pathway 26 to an off-load position at the rearward end 38 of the input queue pathway 26. Tested samples that have been analyzed by the sample analysis system are placed on the output queue pathway 28 for movement from the rearward end 42 of the output queue pathway 28 forwardly toward the workstation area 34 for unloading and other processing or disposal.

The stat shuttle 10 allows an operator to automatic interrupt the usual operation of the input queue 26 of the sample handler 20 to permit automatic preferential or priority delivery of a patient sample or analysis ingredient to the sample analysis system for immediate analysis or usage independent of the input queue pathway 26. The stat shuttle 10 also permits immediate delivery to a sample analysis system of reagent components for reaction with sample, and diluent components for predilution of sample.

The sample handler module 20 further includes a control console 48 located in a tower assembly 50 (FIG. 1) that permits an operator to temporarily interrupt movement of sample tube racks on the input queue pathway 26 while activating the stat shuttle 10. An electronic control system 54 (FIG. 1) that does not form a part of the invention is located below the workstation area 34 for controlling the operation of the sample handler module 20.

In some instances it may not be necessary to stop the input queue while the stat shuttle 10 is activated.

Referring to FIGS. 2, 3, 10 and 13 the adapter 12 includes a carrier housing 60 with a base portion 64 and a peripheral wall 66 extending upwardly from the base portion 64. The peripheral wall 66 has an outside male surface 68 and an inside female surface 72. The peripheral wall 66 includes sidewall sections 76 and 78 and front and rear end sections 83 and 85 of the carrier housing 60. A boss-like key formation 82 is provided on the outside male surface 68 at the front end section 83 whereas the opposite rear end section 85 is keyless.

A pair of spaced key projections 86 are formed on the inside female surface 72 at the sidewall sections 76 and 78 proximate the front end 83 of the carrier housing 60. A similar pair of spaced key projections 90 are formed on the inside female surface 72 at the sidewalls 76 and 78 proximate the rear end 85 of the carrier housing 60.

Figure 15:
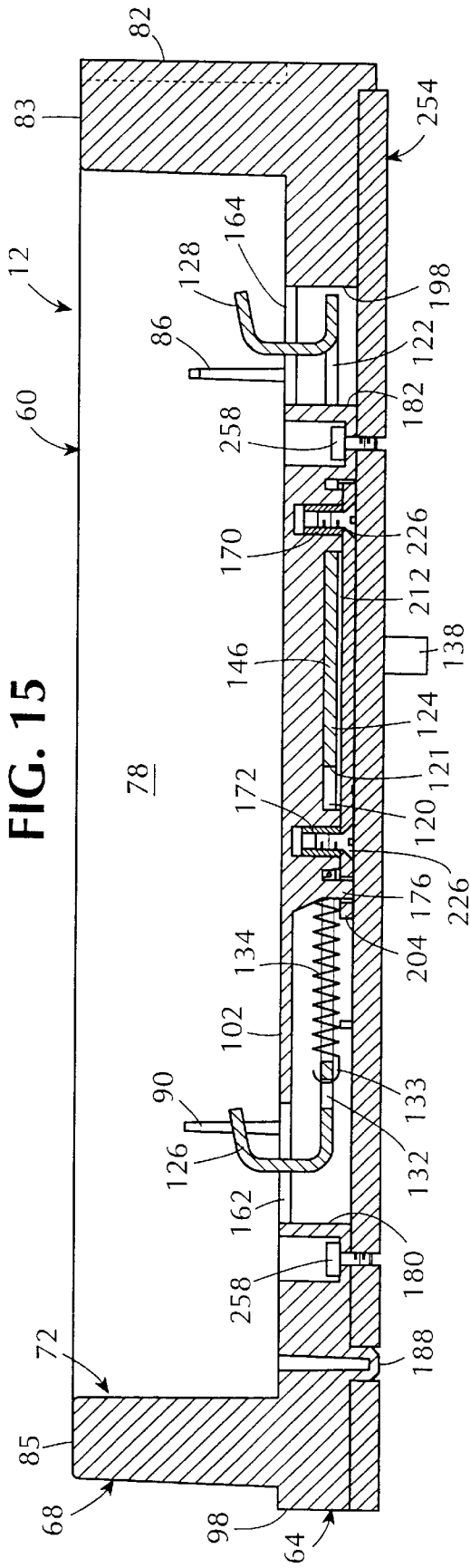
FIG. 15 is a sectional view taken on the line 15—15 of FIG. 14 showing the latch device thereof biased to a normal lock position.

As most clearly shown in FIG. 15, for example, the key projection 86 is spaced a lesser amount from the front end 83 of the carrier housing 60 than the key projection 90 is spaced from the rear end 85 of the carrier housing 60. This spacing difference between the key projections 86, 90 at the front and rear ends 83, 85 serves a keying function for the racks 380 inserted into the female space defined by the female surface 72.

Figure 13:
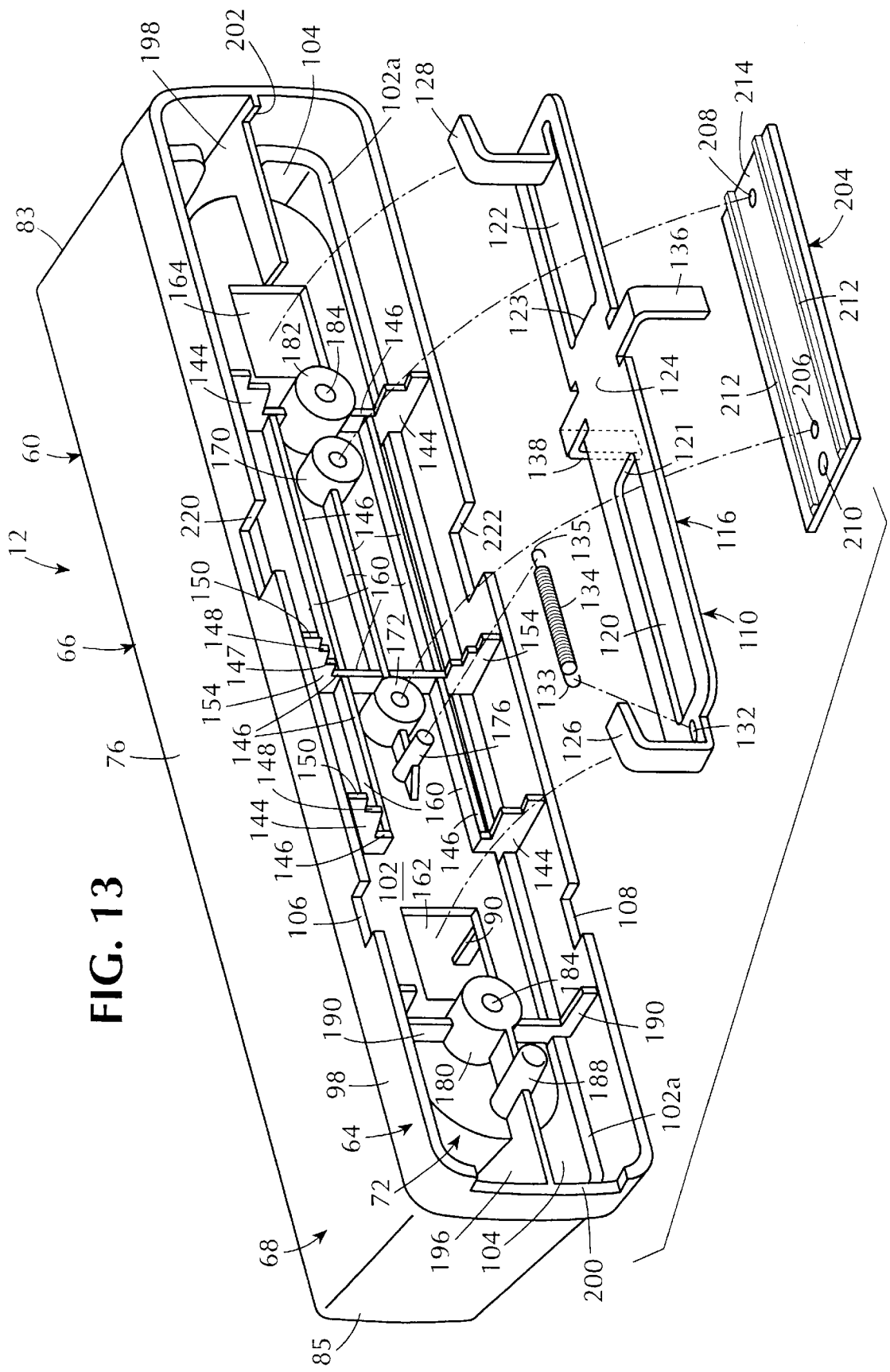
FIG. 13 is an exploded view thereof.

Referring to FIG. 13 the base portion 64 of the carrier housing 60 includes a peripheral base wall 98, a base floor 102 and a space 104. The space 104 hollows out the male portion 68 and defines a marginal base portion 102a which, for purposes of simplicity, will also be referred to as the base floor 102. A latch device 110 is mounted below the base floor 102 for slideable back and forth movement relative to the base floor 102. The term back and forth movement of the latch device 110 is intended to refer to movement toward and away from the front and rear ends 83 and 85 of the carrier housing 60.

Referring again to FIG. 13 the latch device 110 includes an elongated plate portion 116 having spaced clearance openings 120 and 122. The clearance opening 120 is longer but narrower than the clearance opening 122. A pair of latch fingers 126 and 128 are provided at opposite end portions of the latch device 110. A spring securement opening 132 is formed in the plate portion 116 just below the latch finger 126 for securement of one end 133 of a biasing spring 134. A latch actuator in the form of spaced actuator members 136 and 138, depend from the plate portion 116, between the clearance openings 120 and 122.

Referring again to FIG. 13 the carrier housing base floor 102 and the base wall 98 are reinforced with four stepped gussets 144 having steps 146, 148 and 150. Two of the gussets 144 are below the sidewall 76, and two of the gussets 144 are below the opposite sidewall 78. A reinforcing gusset 154 is formed intermediate each pair of gussets 144 and has steps 146, 147, 148 and 150. The reference numbers of the steps 146, 148 and 150 in the gussets 144 and 154 are intended to indicate a similar distance from the base floor 102. The gussets 144 and 154 extend into the hollow space 104 to further reinforce the structure of the carrier housing 60.

A parallel and perpendicular network of web-like formations 160 on the base floor 102 between the latch finger openings 162 and 164 have an end surface 146 that is the same distance from the base floor 102 as the steps 146 on the gussets 144 and 154. The steps 146 and the web surfaces 146 define a guide plane for movement of the latch device 110 which is confined for slideable movement between the steps 148 of the gussets 144 and the steps 147 of the gussets 154.

The carrier housing base floor 102 is also formed with a pair of spaced bosses 170 and 172 having internal threads. The bosses 170 and 172 are connected by at least one of the web-like formations 160. A spring engagement post 176 is provided next to the boss 172 to secure the opposite end 135 of the spring 134. The base floor 102 also includes spaced hollow bosses 180 and 182 proximate each of the latch finger openings 162, 164. A fastener opening 184 is formed in each of the bosses 180 and 182.

A locating pin 188 is provided on the base portion 102 between the securement boss 180 and the end portion 85 of the carrier housing 60 for locating the adapter 12 on the transport device 14. The locating pin 188 extends slightly below the peripheral wall 98. A pair of step-shaped reinforcement gussets 190 are provided on opposite sides of the boss 180. An end gusset 196 on the base platform 102 at the end 85 of the carrier housing 60 reinforces the securement boss 180 and the locating pin 188. An end gusset 198 is provided on the base portion 102 at the opposite end 83 of the carrier housing 60 and extends to the latch finger opening 164.

The adapter 12 further includes a generally rectangular securement member 204, preferably formed of plastic for securing the latch device 110 in a slideable position relative to the base portion 102 of the carrier housing 60. The securement member 204 includes securement openings 206 and 208 and a location opening 210. A pair of spaced and parallel slide rails 212 are formed on a surface 214 of the securement member 204.

The adapter 12 is assembled by placing the plate portion 116 of the latch device 110 on the surfaces 146 of the gussets 144, 154 and the web-like network 160. The plate 116 is positioned such that the latch fingers 126 and 128 pass through the latch finger openings 162 and 164 of the base portion 102. Under this arrangement an imperforate portion 124 of the plate 116 between the clearance openings 120 and 122 is located between the bosses 170 and 172. The latch device 110 is thus capable of sliding back and forth on the carrier housing 60 to a first limit position wherein an edge portion 123 of the clearance opening 122 abuts against the boss 170, to locate the latch fingers 126 and 128 in the lock position. The latch device 110 is also slideable in an opposite direction to a second limit position wherein an edge 121 of the clearance opening 120 abuts against the boss 172 to locate the latch fingers 126 and 128 in the unlock position.

The latch finger openings 162 and 164 in the base portion 102 are sized to accommodate back and forth movement of the latch fingers 126 and 128 without interference. With the plate portion 116 of the latch device 110 thus located at the base portion 102 of the carrier housing 60, the spring end 133 is secured in the spring securement opening 132 at the latch finger 126 and the opposite spring end 135 is secured around the spring post 176. Under this arrangement the elongated plate portion 116 of the latch device 110 is normally biased to the lock position wherein the edge 123 of the clearance opening 122 abuts the boss 170.

Figure 14:
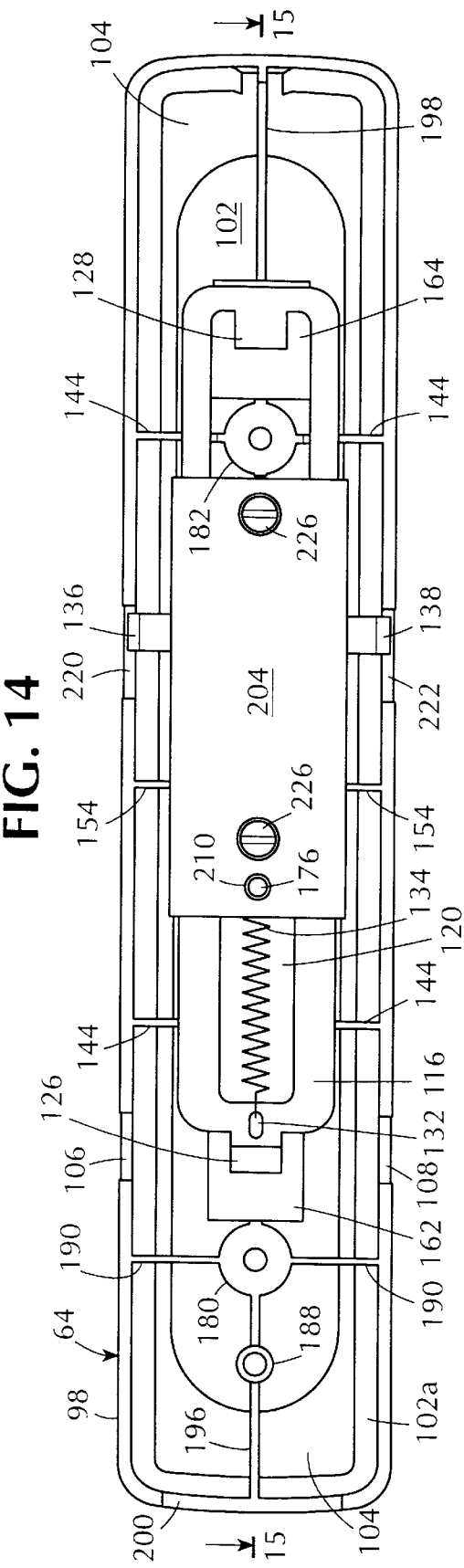
FIG. 14 is a bottom view thereof.

The peripheral base wall 98 of the carrier housing 60 further includes cutout portions 220, 222 which align with the respective actuator members 136 and 138 of the latch device 110. The cutout portions 220, 222 are sized to accommodate back and forth movement of the actuator members 136 and 138 without interference. The securement member 204 is positioned at the base portion 102 of the carrier housing 60 such that the post opening 210 aligns with and snugly receives the spring post 176 at the base portion 102. Under this arrangement the spring end 135 around the spring post 176 is confined between the base platform 102 and the securement member 204. Also, under this arrangement the fastener openings 206 and 208 in the securement member 204 are aligned with the internal threaded openings of the bosses 170 and 172 to permit fastening of the securement member 204 onto the bosses 170 and 172 with suitable threaded fasteners such as 226 (FIG. 14).

It should be noted that the elevation of the bosses 170 and 172 from the base portion 102 is an amount which will provide clearance between the securement member 204 and the plate portion 116 of the latch device 110. Thus no force is imposed by the securement member 204 against the plate portion 116 thereby permitting free sliding movement of the plate portion 116 back and forth from the normal spring biased lock position to the unlock position. With the latch device 110 thus secured to the carrier housing 68 the actuator members 136 and 138 of the latch device 110 depend from the cutout portions 220 and 222 in the manner shown in FIG. 10.

Figure 7:
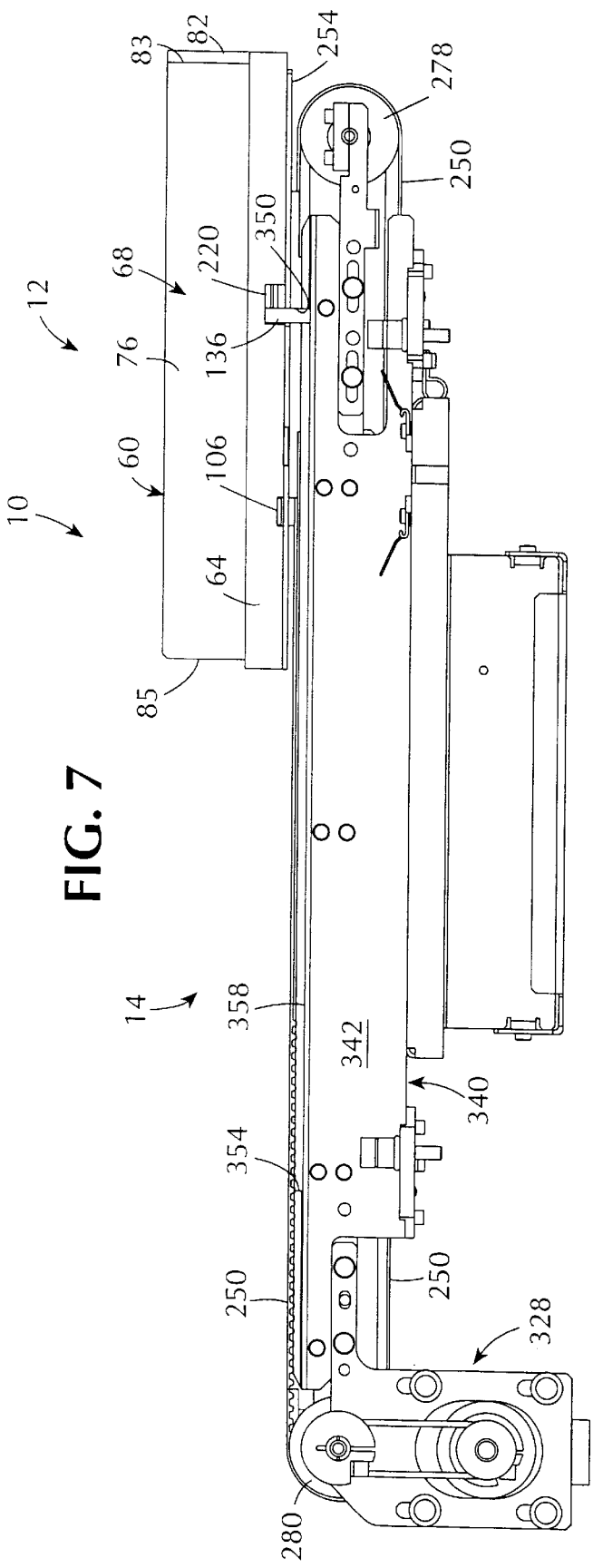
FIG. 7 is a side elevational view thereof.

Referring to FIG. 3 the adapter 12 is transported back and forth by the transport device 14 from a forward load position as shown in FIG. 7 to a rearward unload position as shown in FIG. 3 and vice versa.

Figure 5:
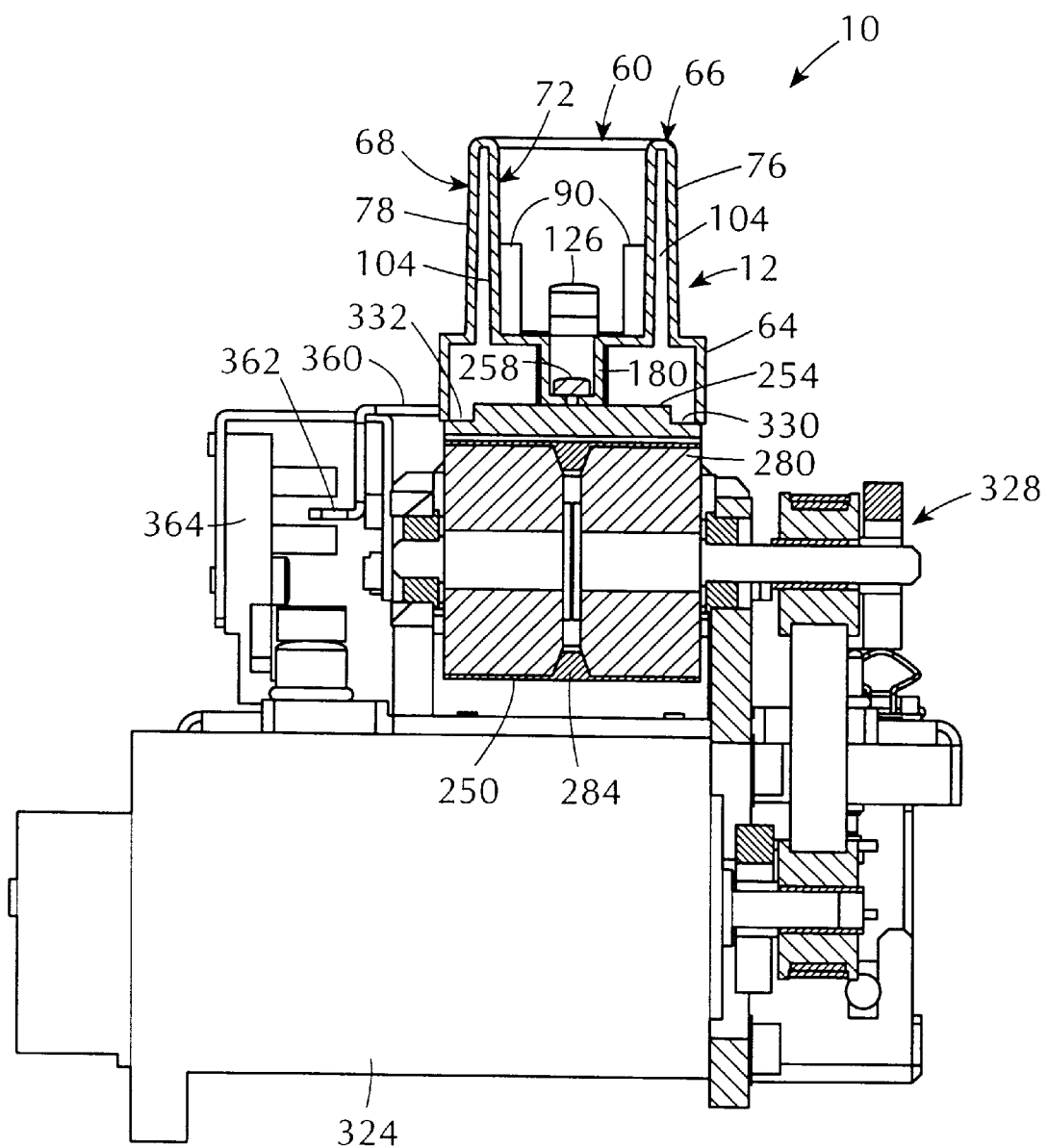
FIG. 5 is an end view partially shown in section, taken on the line 5—5 of FIG. 3.

The adapter 12 is secured to a conveyor belt or timing belt 250 of the transport device 14 with an attachment platform 254 (FIGS. 3 and 3A). The adapter 12 is secured to the attachment platform by means of a fastener 258 provided in each of the securement bosses 180 and 182 in the manner shown in FIG. 5 to engage respective threaded openings 264, 262 (FIG. 3A) in the attachment platform 254. When the adapter 12 is thus fastened to the attachment platform 254 the locating pin 188 (FIG. 13) of the carrier housing 60 snugly engages the pin opening 266 (FIG. 3A) of the attachment platform 254.

The conveyor or timing belt 250 is not an endless belt but has belt end portions 270 and 272 (FIG. 3D) that are of reduced width relative to the portions of the conveyor belt 250 that ride upon the pulleys 278 and 280 (FIG. 3) provided at opposite ends of the transport device 14. The conveyor belt 250 includes a spline 284 (FIG. 3D) that engages a complementary shaped circumferencial groove 285 (FIG. 3A) in the pulleys 278 and 280. Conveyor belt teeth 286 (FIG. 3D) are provided on opposite sides of the spline 284 for the full length of the conveyor belt 250. Belt teeth 286 are also provided on the belt end portions 270 and 272.

Figure 3D:
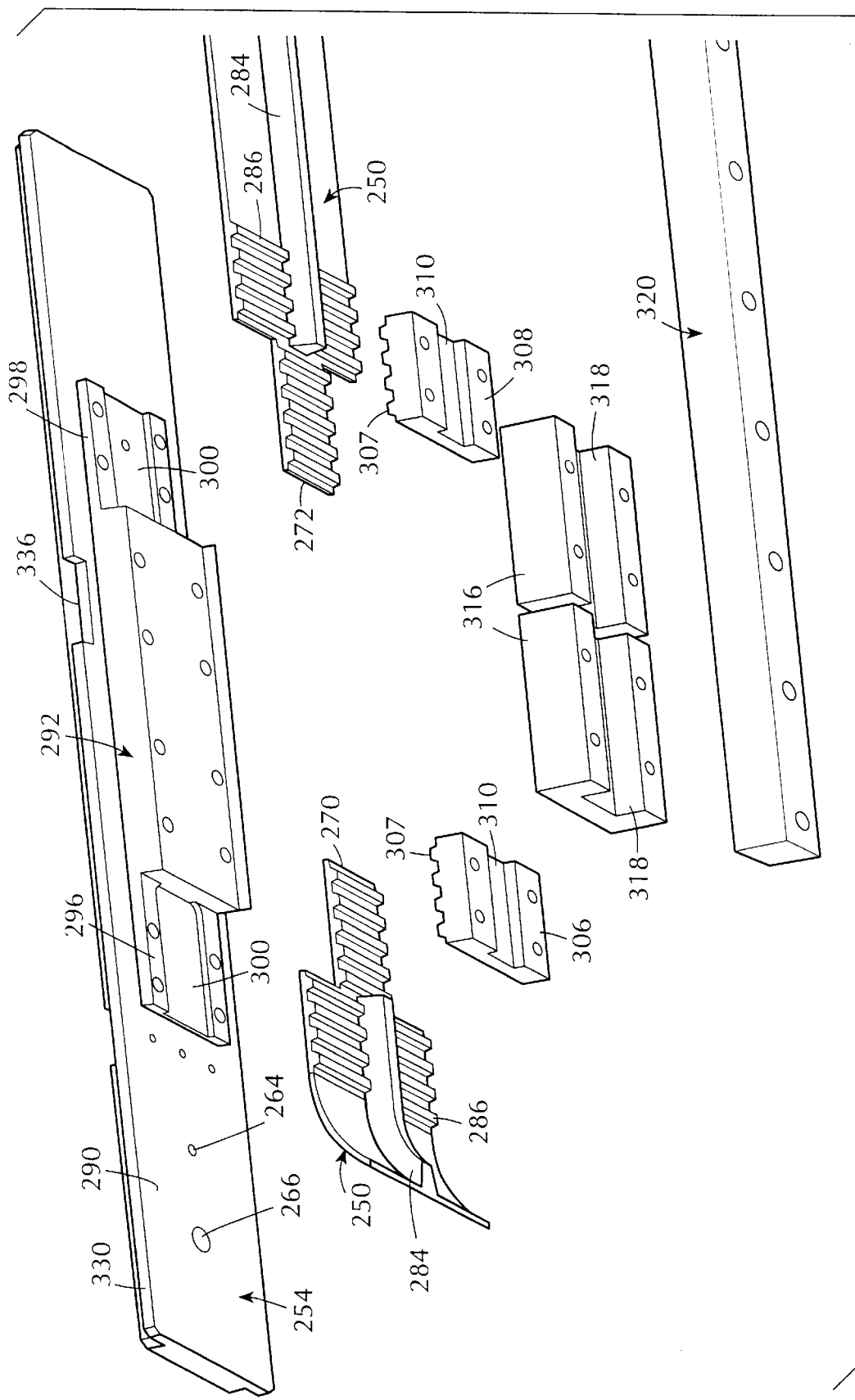
FIG. 3D is an exploded view of FIG. 3B.
Figure 4:
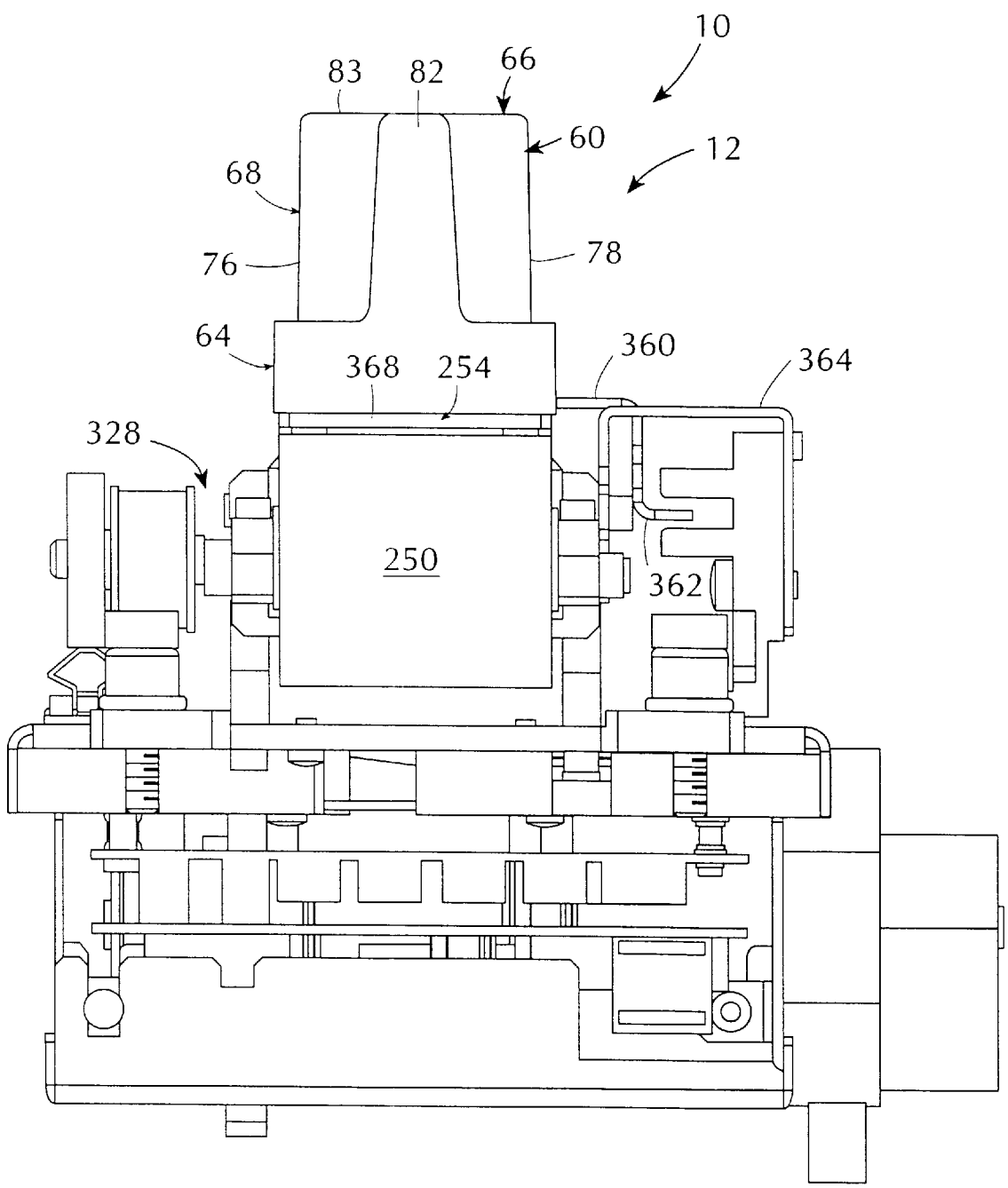
FIG. 4 is an end view taken on the line 4—4 of FIG. 3.

Referring to FIG. 3D the attachment platform 254, which is preferably formed of metal such as aluminum has an underside 290 that is formed with a securement section 292. The securement section 292 has opposite step down end portions 296 and 298 with shallow channels 300 for accommodating the belt end portions 270 and 272. A timing belt clamp 306 with tooth formations 307 that are complementary to the conveyor belt teeth 286 fastens the belt end portion 270 to the step down end portion 296 of the attachment platform 254. A similar timing belt clamp 308 secures the belt end portion 272 to the step down end portion 298 of the attachment platform 254. Each of the timing belt clamps has a clearance channel 310.

Still referring to FIG. 3D a pair of bearing members 316 are also secured to the securement section 292 between the step down end portions 296 and 298. The bearing members 316 have roller members (not shown) in a channel portion 318. The bearing members 316 are a suitable known structure such as IKO part number LWL12C2R435H/M3 sold by IKO International Inc. of Parsippany, N.J. The bearing channel 318 engages a guideway 320 such that the back and forth movement of conveyor belt 250 results in roller bearing sliding movement of the attachment platform 254 on the guideway 320.

The conveyor belt 250 is driven by a suitable known stepper motor 324 (FIG. 5) which is drivingly engaged with the pulley 280 through a suitable arrangement of drive belts and pulleys that are generally indicated by the reference number 328.

Referring to FIG. 3A the transport device 14 further includes a frame 340 with opposite sidewalls 342 and 344. Each of the sidewalls 342 and 344 has an upper elongated rail surface on which the flexible portion of the conveyor belt 250 rides. The guideway 320 for the attachment platform 254 is located between the sidewalls 342 and 344.

Still Referring to FIG. 3A a step-like formation 350 in each of the sidewalls 342 and 344 proximate the pulley 278 forms a first hard stop or actuator member engagement surface for the actuator members 136 and 138 of the latch device 110 of the adapter 12. A symmetrical step-like formation 354 is also formed in the rail surfaces 346 of the sidewalls 342 and 344 proximate the pulley 280. The step-like formation 354 forms a hard stop or actuator member engagement surface at a rearward end of the conveyor for potential engagement with the actuator members 136 and 138 of the adapter 12. A clearance channel 358 is formed in the sidewalls 342 and 344 between the step-like formations 350 and 354 at the rail surface 346.

Referring to FIG. 13 the peripheral base wall 98 of the carrier housing 60 has a recess 200 below the end portion 85, and the end gusset 198 has a step 202 below the end portion 83 of the carrier housing 60. The peripheral base 98 also includes a shallow recess 106 below the sidewall 76 and a similar oppositely disposed shallow recess 108 below the sidewall 78. Referring to FIG. 3A the attachment platform 254 includes elongated marginal steps 330 and 332 at opposite edges of an upper surface 334 of the platform. A clearance recess 336 is provided in each marginal step 330 and 332 for accommodation of the respective actuator members 136 and 138 (FIG. 13) of the adapter 12. A channel 338 (FIG. 3A) is formed in the upper surface 334 of the attachment platform for securement of a flag member 360 having a signaling projection 362. A flag sensor 364 is secured to the sidewall 344 of the conveyor frame 340.

Figure 10:
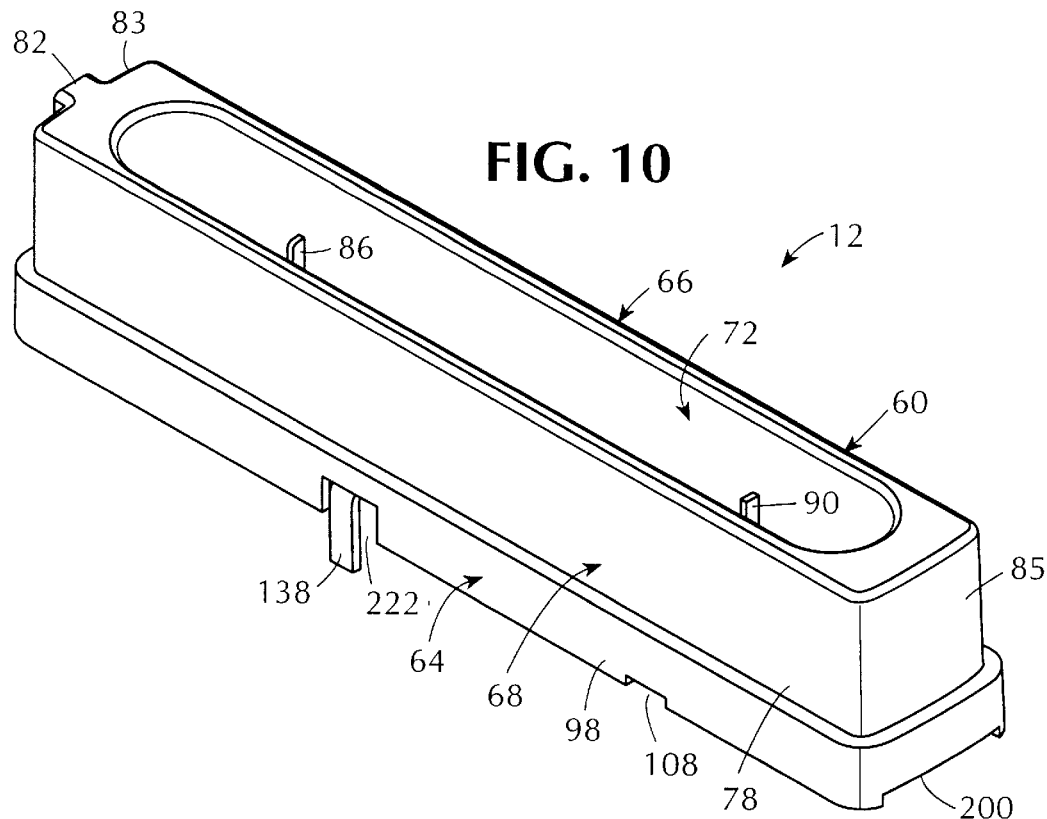
FIG. 10 is a simplified schematic perspective view of the stat shuttle adapter.
Figure 11:
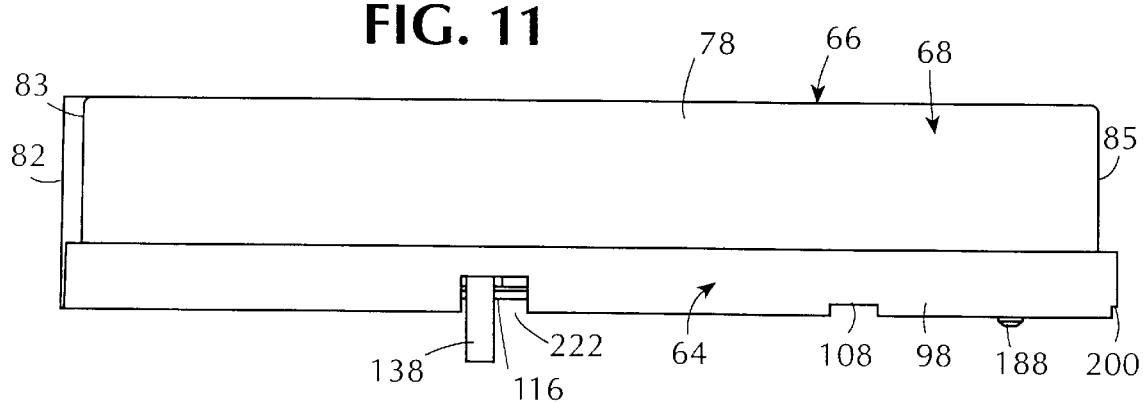
FIG. 11 is a front elevational view thereof.
Figure 12:
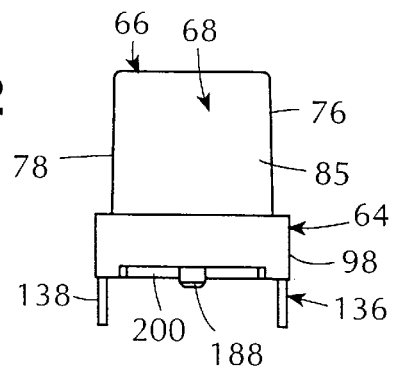
FIG. 12 is an end view thereof taken from the right side of FIG. 11.

Referring to FIGS. 3A, 10 and 13 when the adapter 12 is secured to the platform 254 the step 202 at the forward end 83 of the carrier housing 60 engages a forward end 368 of the attachment platform 254. The clearance recess 200 at the rear end 85 of the carrier housing 60 spans the upper surface 334 of the platform 254 between the marginal steps 330 and 332. The shallow recesses 106 and 108 provide clearance for the carrier housing 60 relative to the flag member 360. The recesses 336 in the marginal steps 330 and 332 of the attachment platform 254 provide clearance for the actuator members 136 and 138 to enter the clearance channel 358 of the frame sidewalls 342 and 344 in the step-like formations 350 and 354 in each of the sidewalls 342 and 344.

When the adapter 12 is positioned on the conveyor belt 250 between the step-like formations 350 and 354 (FIGS. 3 and 3A) the latch device 110 is normally biased by the spring 134 into the lock position (FIG. 15). With the latch device in the lock position, the edge 123 (FIG. 13) of the clearance opening 122 abuts the boss 170 of the base platform 102.

Figure 6:
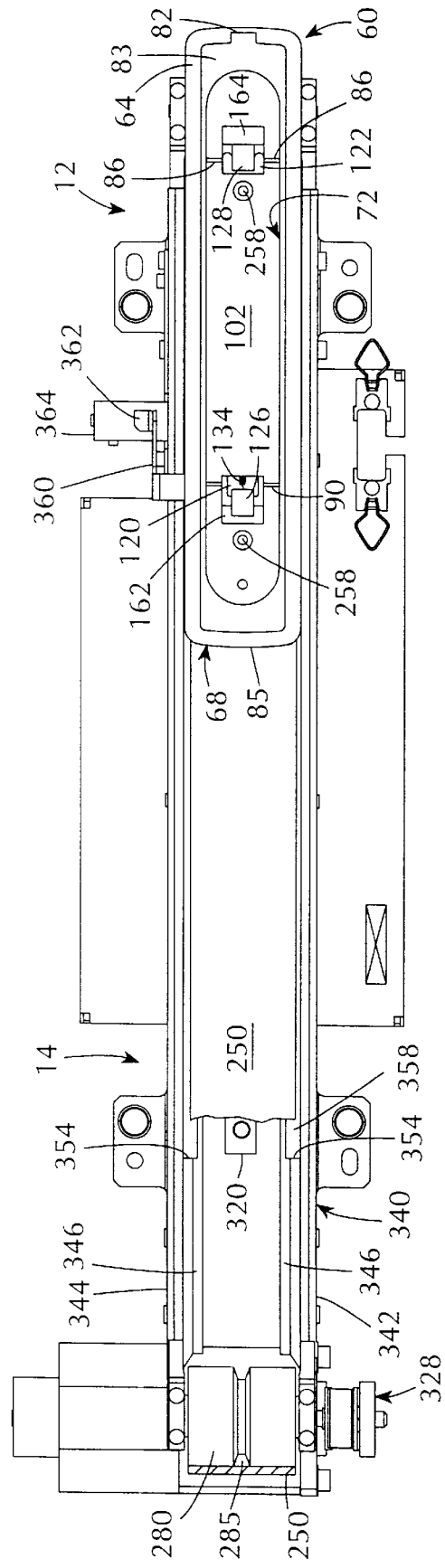
FIG. 6 is a top plan view showing the stat shuttle adapter at a forward load position on the transport device.
Figure 8:
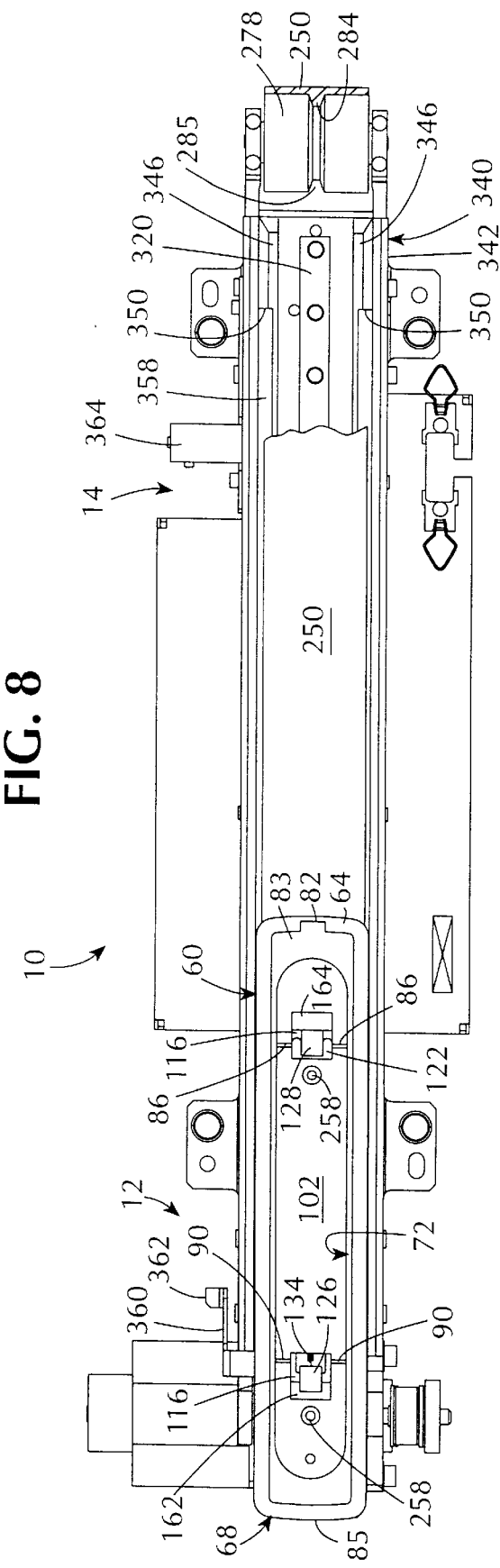
FIG. 8 is a top plan view thereof with the stat shuttle adapter in the rearward unload position.
Figure 17:
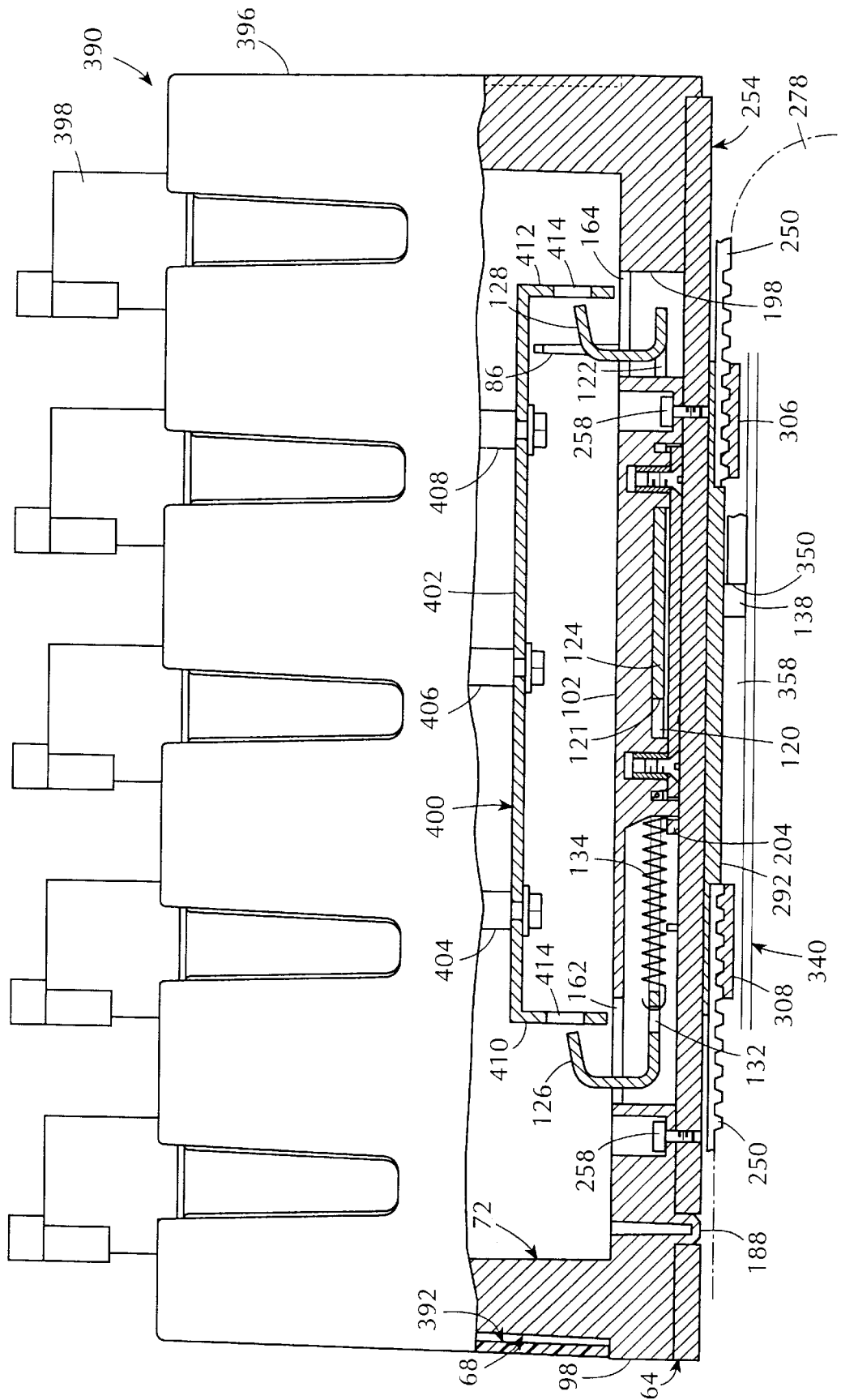
FIG. 17 is a front elevational view thereof at a forward load position on the transport device and showing the stat shuttle adapter latch device in the unlock position with a rack for diluent packages mounted thereon.
Figure 19:
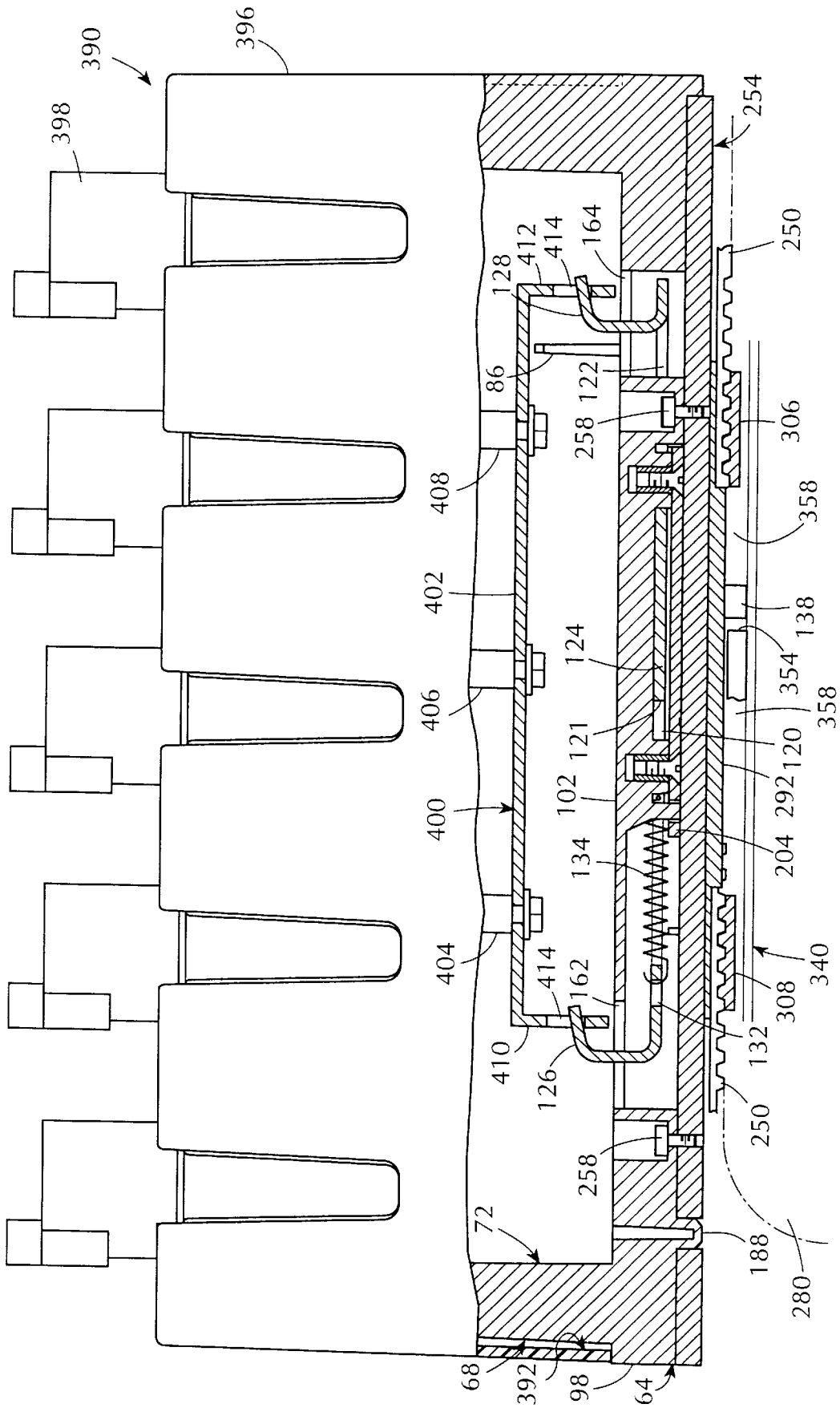
FIG. 19 is a view similar to FIG. 18 showing the stat shuttle adapter latch device in the lock position with the stat shuttle adapter at the rearward unload position on the transport device.

With the adapter 12 thus secured to the attachment platform 254 of the transport device 14 the conveyor belt 250 is movable by the motor 324 in opposite directions for a predetermined bi-directional movement of the adapter 12. Thus the transport device 14 is operable in any suitable known manner to bring the adapter 12 to a forward load position as shown in FIGS. 6 and 17 can be determined when the signal projection 362 (FIGS. 5 and 6) of the flag member 360 aliens with and activates the flag sensor 364 at the forward end of the transport device 14. Movement of the conveyor belt 250 in an opposite direction to place the adapter 12 in a rearward unload position as shown in FIGS. 3, 8 and 19 is accomplished by operating the stepper motor 324 for a predetermined number of steps that correspond to the location of the adapter 12 in a predetermined rearward position on the transport device 14.

Figure 16:
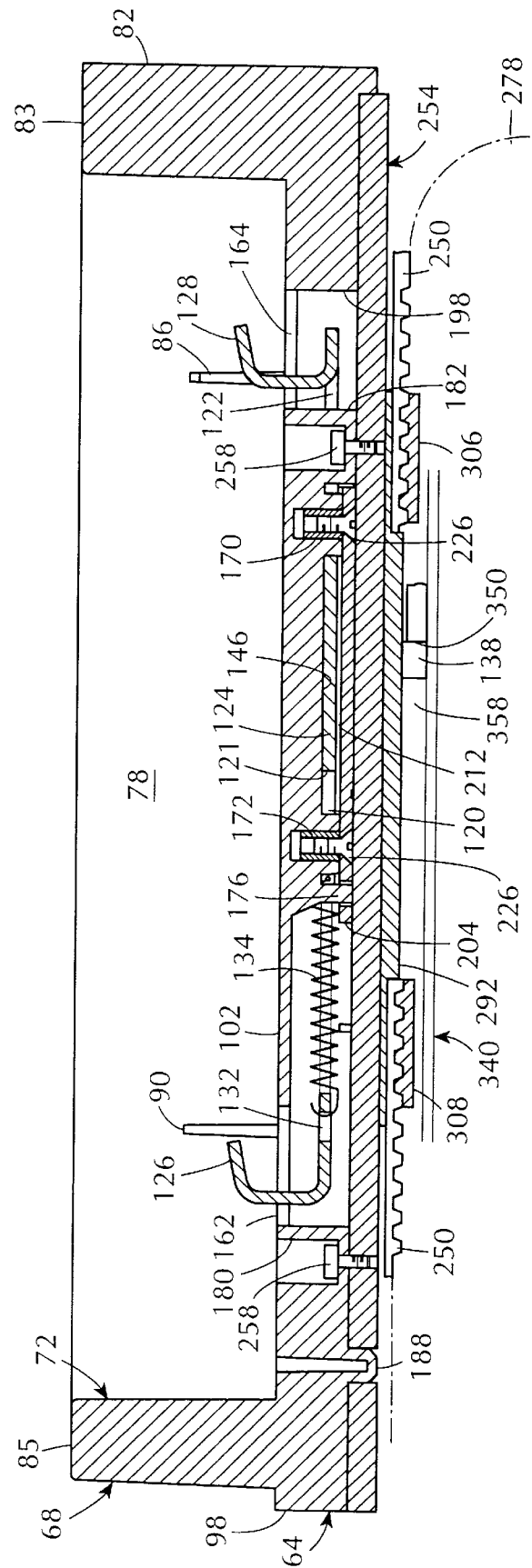
FIG. 16 is a sectional view thereof corresponding to FIG. 15 at a forward load position on the transport device and showing the stat shuttle adapter latch device in an unlock position.

When the adapter 12 is in the forward load position of FIG. 17 the latch engagement surface 350 (FIG. 3A) of the transport device 14 engages the actuator members 136 and 138 (FIG. 13) to cause the latch device 110 to shift rearwardly from its normally biased lock position as shown in FIG. 15 to the unlock position as shown in FIG. 16. Thus as long as the latch engagement surface 350 (FIG. 3A) remains in contact with the latch actuator members 136 and 138 (FIG. 13) while the adapter 12 is in the forward load position the latch device 110 will remain in the unlock position as shown in FIG. 16.

When the adapter 12 is in the forward load position of FIG. 17 and the latch device 110 is in the unlock position a sample tube rack 380 (FIG. 27) a diluent container rack 390 (FIG. 21) or a reagent package rack 450 (FIG. 24) can be loaded onto the adapter 12 in easy drop in fashion without the need to apply any force or overcome any resistance by the adapter 12.

Figure 21:
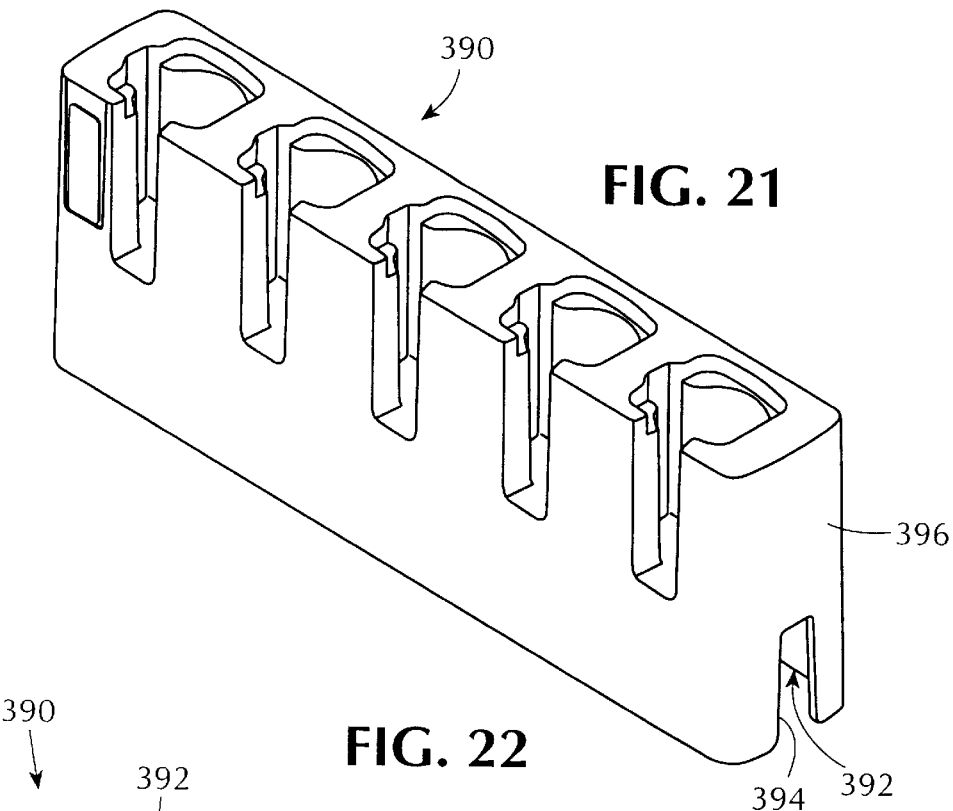
FIG. 21 is a perspective view of a diluent rack.
Figure 22:
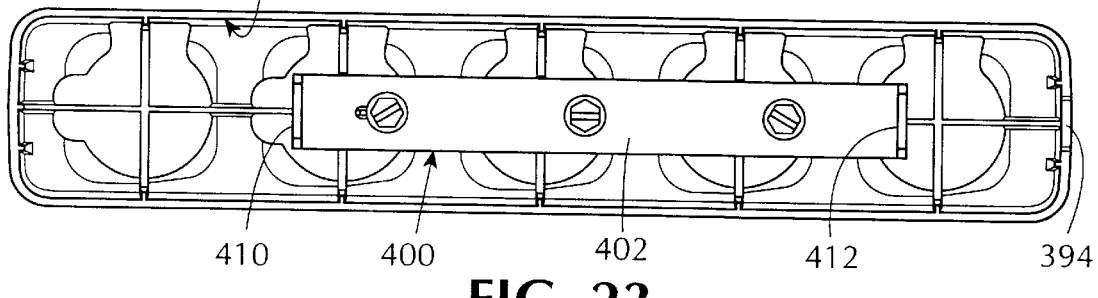
FIG. 22 is a bottom view thereof.
Figure 23:
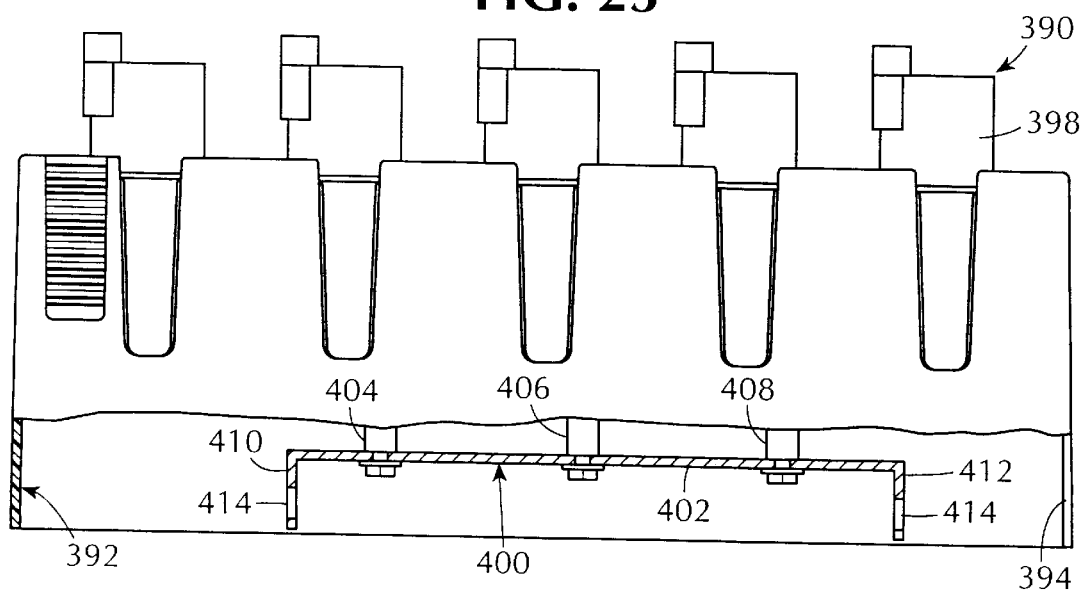
FIG. 23 is a front elevational view thereof, partly shown in section.

For example, referring to FIGS. 10, 17 and 21 the diluent package rack 390 includes an internal female surface 392 that is of complementary shape with the external male surface 68 of the adapter 12. The diluent package rack 390 further includes a key recess 394 and a front end 396 that is of complementary shape with the key formation 82 at the front end of the adapter 12. A "U" shaped latch member 400 is secured to the rack 390 within the female space 392 in any suitable known manner as by securing a median portion 402 (FIG. 22) of the latch member 400 to bosses 404, 406 and 408 (FIG. 23) that are formed within the female cavity 392 of the rack 390. The latch member 400 includes opposite depending legs 410 and 412 (FIG. 23) which each include a latch finger opening 414. When the adapter 12 is in the load position as shown in FIG. 17 the latch member 400 is positioned within the female space 392 of the rack 390 such that the latch finger openings 414 are free from engagement with the latch fingers 126 and 128 of the latch device 110.

Figure 9:
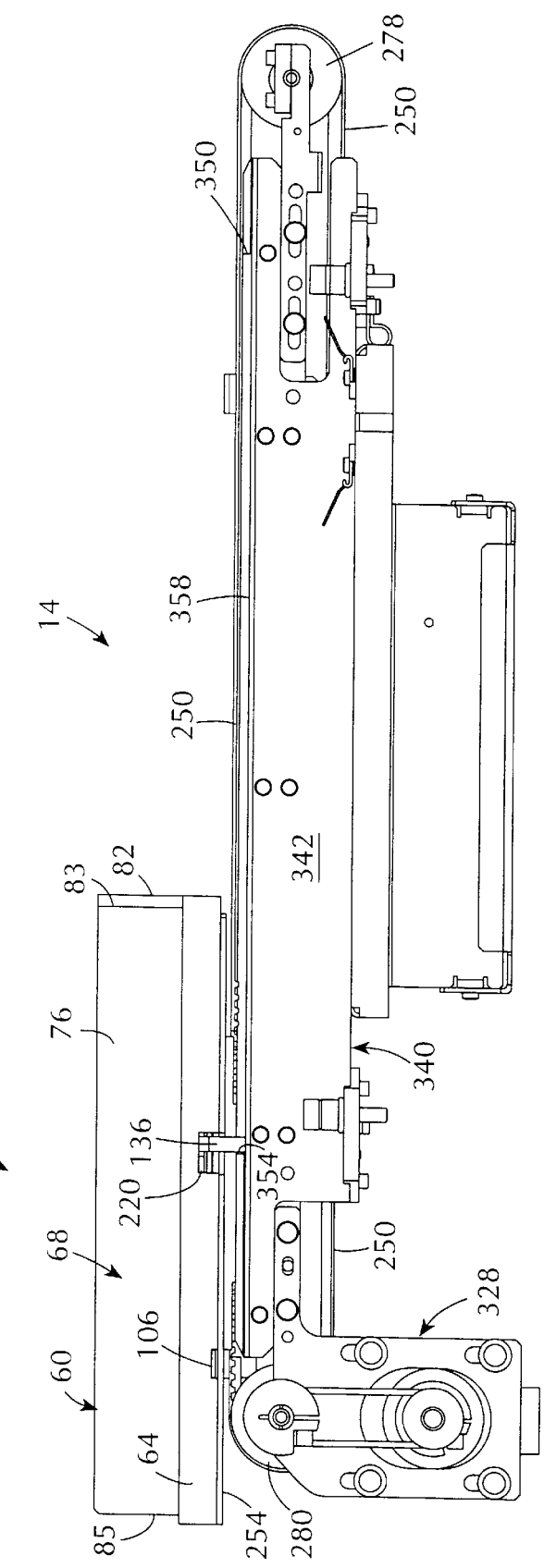
FIG. 9 is a front elevational view thereof.
Figure 18:
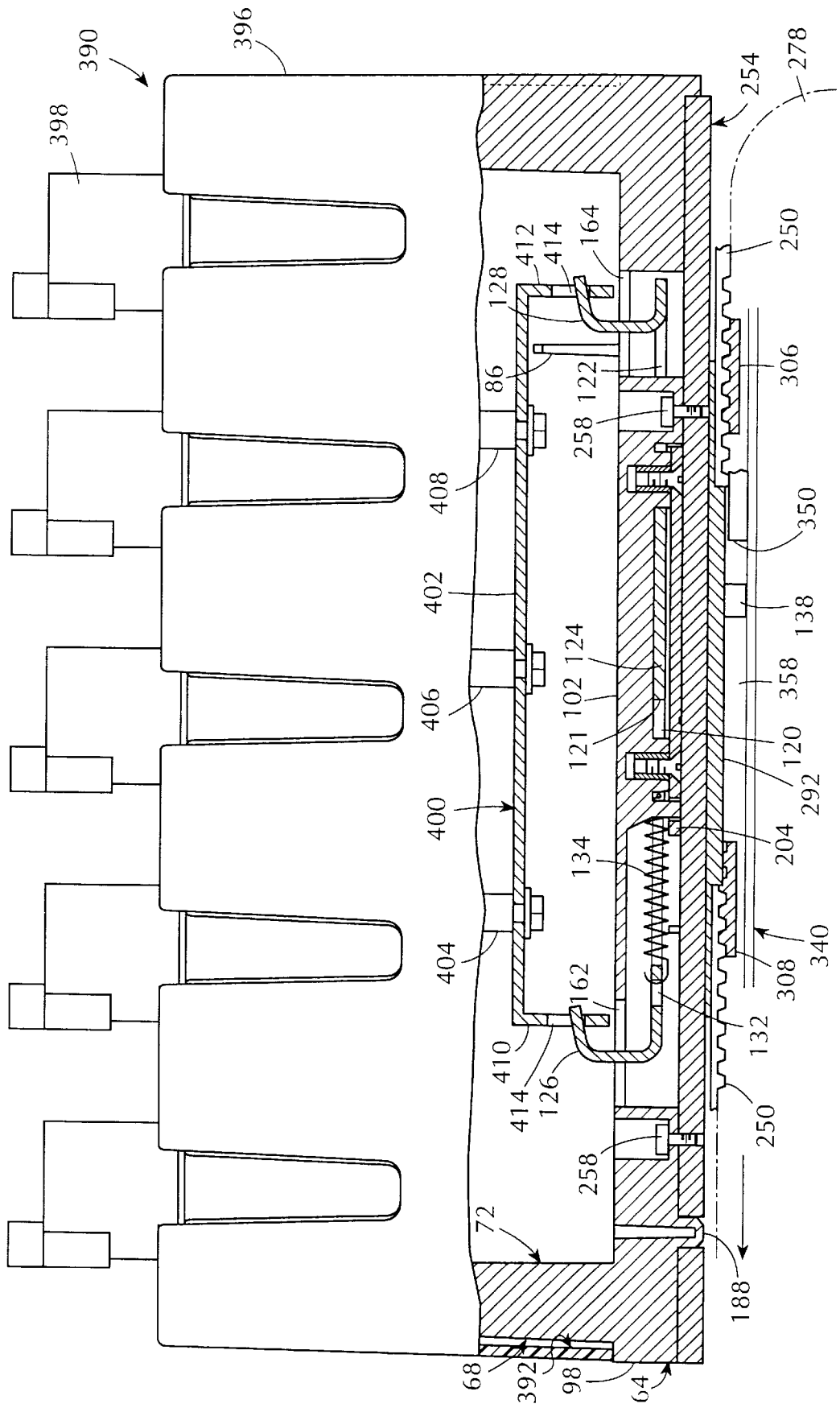
FIG. 18 is a view corresponding to FIG. 17 with the stat shuttle adapter latch device in a lock position, as the transport device moves the stat shuttle adapter away from the forward load position to the rearward unload position.

As the conveyor belt 250 transports the adapter 12 from the forward load position of FIG. 7 toward the rearward unload position of FIG. 9 the actuator member 136 and the unshown actuator member 138 clear the latch engagement surface 350 (FIG. 18) of the transport device 14 enabling the biasing spring 134 to bias the latch device 110 of the adapter 12 into the lock position as shown in FIG. 18. When the latch device 110 is in the lock position the latch fingers 126 and 128 enter the latch finger openings 414 of the latch member 400 and lock the rack 390 to the adapter 12.

As long as the latch 110 of the adapter 12 remains in the lock position during transport of the adapter 12 to the rearward unload position the latch actuator 136 and 138 will not engage the engagement surface 354 at the rearward portion of the transport device 14 (FIG. 19).

Figure 20:
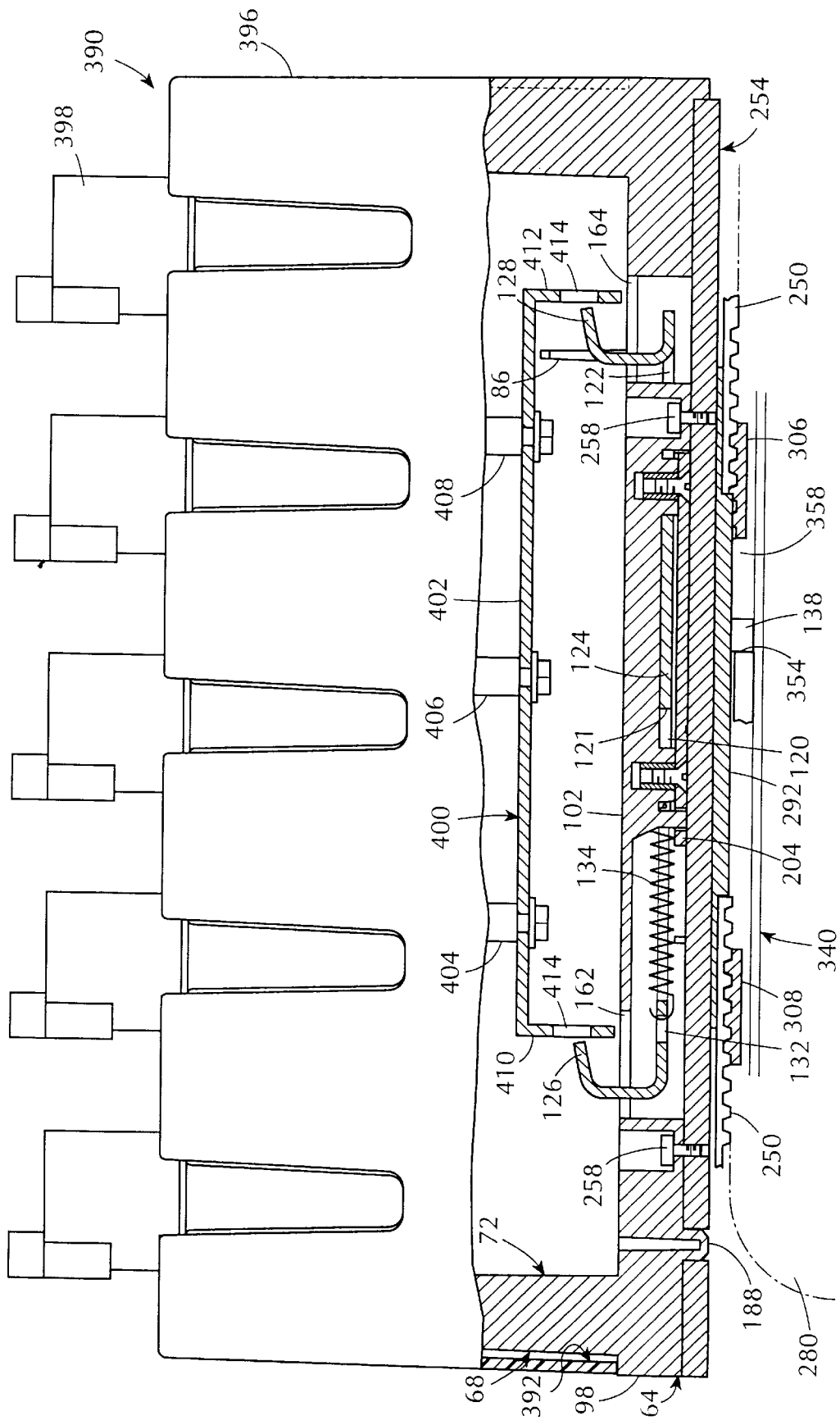
FIG. 20 is a view similar to FIG. 19 showing the stat shuttle adapter latch device in an unlock position as the adapter approaches the rearward unload position.

However if the latch device 110 is inadvertently stuck or jammed in the unlock position of FIG. 17 as the conveyor belt 250 moves the rack 390 from the forward load position to the rearward unload position the actuator member 136 will engage the engagement surface 354 (FIG. 20) as the adapter 12 approaches the rearward unload position. Engagement between the actuator member 136 and the latch engagement surface 354 at the rearward unload position will cause the latch device 110 to move into the lock position of FIG. 18. Under this arrangement whenever the adapter 12 is in the unload position any rack carried by the adapter 12, is locked to the adapter 12 to facilitate unloading of a rack such as the rack 390 without causing any movement of the rack 390 relative to the adapter 12.

Once the diluent packages 398 of the rack 390 have been unloaded at the rearward unload position of the transport device 14 the diluent packages 398 can immediately enter the sample analysis system (not shown) thereby preempting the normal input queue of test samples on the input passageway 26.

Reverse movement of the conveyor 250 moves the unloaded rack 390 back to the forward load position of the transport device 14 wherein the latch device 110 of the adapter 12 is once again placed in the unlock position (FIG. 17). With the latch device in the unlock position the rack 390 can be removed from the adapter 12 without any force since there is no locking engagement between the latch device 110 and the rack 390. The empty rack 390 can be replaced with another rack 390 containing diluent containers if needed for immediate transport to the sample analysis system or the stat shuttle adapter and transport device 10 can be deactivated at the control panel 48, for example and the normal input queue of test samples on the input pathway 26 can be reactivated at the control panel 48.

Figure 24:
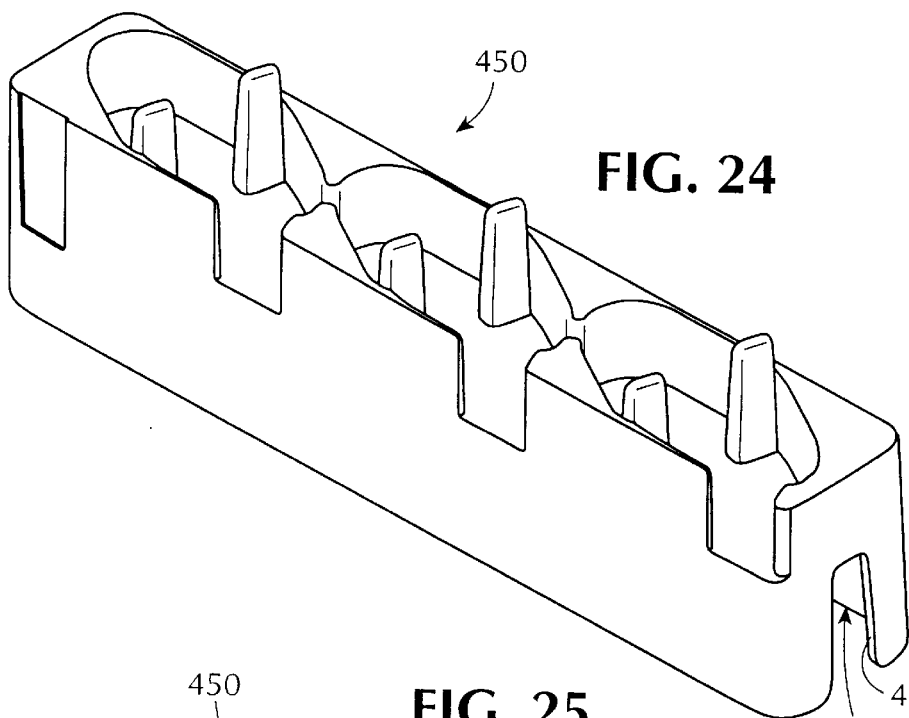
FIG. 24 is a simplified schematic perspective view of a reagent rack.
Figure 25:
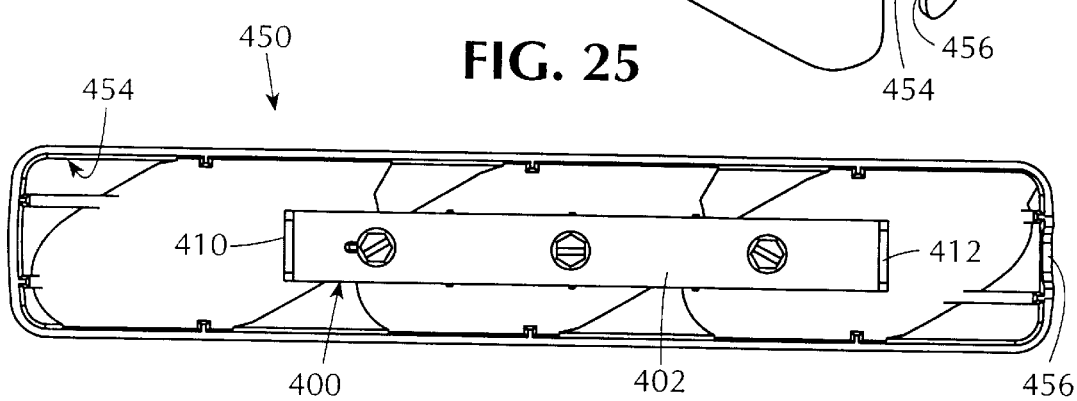
FIG. 25 is a bottom view thereof.
Figure 26:
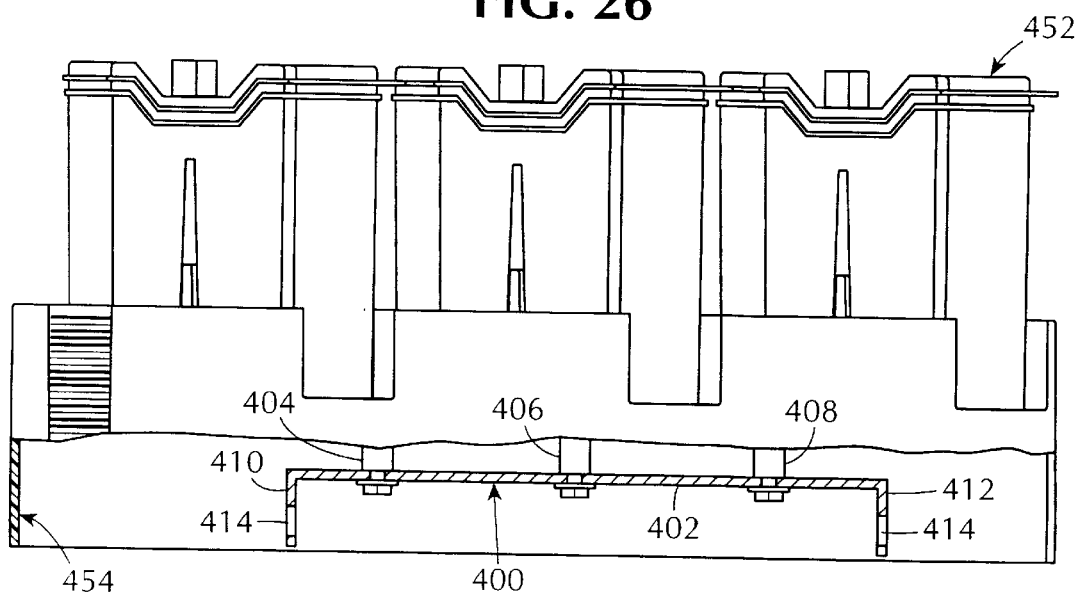
FIG. 26 is a front elevational view thereof, partly shown in section.

If reagent rather than diluent is immediately needed in the sample analysis system the rack 450 (FIGS. 24–26) can be used to transport reagent packages 452 that are held by the rack 450. The reagent rack 450 includes a female space 454 (FIG. 24) similar to the female space 392 of the rack 390. The latch member 400 (FIG. 26) is also secured within the female space 454 in a manner similar to that described for the rack 390. The rack 450 also includes a key recess 456 (FIG. 24). The female space 454 of the rack 450 is of complementary shape with the male surface 68 (FIG. 10) of the adapter 12.

The latch member 400 is positioned within the female space 454 of the rack 450 in a manner that permits force free loading of the rack 450 onto the adapter 12 in a manner similar to that described for the diluent rack 390 when the adapter 12 is in the forward load position of the transport device 14 (FIG. 7). Movement of the rack 450 on the adapter 12 is accomplished in a manner similar to that described for movement of the rack 390 toward the rearward unload position (FIG. 9). The rack 450 is unloaded in a manner similar to that described for unloading of the rack 390. Any inadvertent jamming of the latch device 110 in the unlock position as the rack 450 moves to the rearward unload position of the transport device 14 can be overcome in the manner previously described for overcoming jam-ups of the latch device 110.

Although the latch member 400 is shown as a separate member for the racks 390 and 450 other latch arrangements can be provided for a rack such as the sample tube rack 380 of FIG. 30. The sample tube rack 380 (FIG. 27) includes a male surface 382 that is of complementary shape with the female surface 72 (FIG. 10) of the adapter 12. The rack 380 also includes spaced recesses 384 and 386 (FIG. 27) that serve a keying function. The recesses 384 and 386 align with the key projections 86 and 90 on the female surface 72 of the adapter 12 when a front wall 388 the rack 380 (FIG. 27) is positioned adjacent the wall 76 of the adapter 12. If the front wall 388 of the rack 380 is positioned in the female space of the female surface 72 adjacent the wall 78 (FIG. 10) of the adapter 12 the keying arrangement will misalign. Any misaligned keying arrangement alerts an operator to change the orientation of the rack relative to the adapter.

As most clearly shown in FIG. 29 wall portions 460 and 462 of the respective recesses 384 and 386 in the rack 380 include latch finger openings 464 similar to the latch finger openings 414. Spacing between the latch finger openings 464 is similar to the spacing between the latch finger openings 414 in the racks 390 and 450 of FIGS. 23 and 26.

When the adapter 12 is in the forward load position (FIG. 7) on the transport device 14 and it is desired to immediately transport sample to the sample analysis system the sample rack 380 containing sample tubes 381 (FIG.29) is loaded into the female space 72 (FIG. 10) of the adapter 12 in the manner shown in FIG. 30. The latch device 110 is thus in the unlock position such that the latch fingers 126 and 128 are held away from the latch finger openings 464 by engagement of the actuator members 136 and 138 with the latch engagement surface 350 of the transport device 14. The sample tube rack 380 can thus be easily deposited into the female surface 72 of the adapter 12 without the need for any force.

A force free engagement between any rack and the adapter 12 is a characteristic of the stat shuttle adapter and transport device 10 when the adapter 12 is in the forward load position on the transport device 14.

When the adapter 12 is moved from the forward load position (FIG. 7) to the rearward unload position (FIG. 9) of the transport device 14 the latch actuator members 136, 138 clear the latch engagement surface 350 (FIG. 3A) enabling the latch device 110 to assume its normally biased lock position as shown in FIG. 30.

Upon arrival of the adapter 12 at the rearward unload position of the transport device 14 (FIG. 9) the latch device 110 normally remains in the lock position of FIG. 31 to securely hold the sample rack 380 to the adapter 12 while the sample tubes 381 are unloaded from the sample rack 380. Should there be any inadvertent jamming of the latch device 110 in the unlock position the actuator members 136 and 138 will interfere with the latch engagement surface 354, as previously described, to cause movement of the latch device 110 into the lock position when the adapter 12 is at the rearward unload position. Thus selected sample tube racks 380 can be immediately transported to the sample analysis system without manipulating or otherwise rearranging sample racks in the input queue pathway 26.

When the stat shuttle operation is no longer required an operator can deactivate the stat shuttle at the console 48 in any suitable known manner and reactivate operation of the input queue pathway 26.

Under this arrangement there is no need to manipulate or otherwise handle sample tubes racks in the input pathway 26 in order to allow immediate delivery of a preemptive sample tube rack to the sample analysis system.

A simple expeditious preemptive delivery of sample analysis ingredients to the sample analysis system is thus accomplished without the need for shifting or changing the normal input queue of samples that are awaiting delivery to the sample analysis system.

In view of the above, it will be seen that several objects of the invention are achieved, and other advantageous results attained.

As various changes can be made in the above constructions without departing from the scope of the invention, it is intended that all matter contained in the above description are shown in the accompanying drawings shall be interpreted as illustrative and not in a limiting sense.

What is claimed is:

1. A shuttle adapter device comprising,
    a) a carrier housing having a base portion and an outside male surface extending from said base portion, said outside male surface being of predetermined shape for complementary engagement with an inside female surface of one type of article that can be carried by said carrier housing,
    b) said carrier housing having an inside female surface extending from said base portion, said inside female surface being of predetermined shape for complementary engagement with an outside male surface of another type article that can be carried by said carrier housing, and
    c) a latch device slideably mounted on said carrier housing for slideable movement in opposite directions relative to said base portion from an unlock position free from locking engagement with an article carried by said carrier housing to a lock position in locking engagement with the article, said latch device being normally biased to said lock position.

2. The shuttle adapter device as claimed in claim 1, wherein said latch device includes at least one latch engagement member, engageable with a latch component on an article that can be carried by said carrier housing when said latch device is in said lock position, and said latch engagement member being disengageable from the latch component on an article that can be carrier by said carrier housing when said latch device is in said unlock position.

3. The shuttle adapter device as claimed in claim 2, wherein said base portion includes at least one opening through which said latch engagement member projects.

4. The shuttle adapter device as claimed in claim 3, wherein said latch engagement member projects into a space defined by said inside female surface.

5. The shuttle adapter device as claimed in claim 2, wherein said latch device includes an actuator member for effecting movement of said latch device from the lock position to the unlock position, said actuator member being movable in one direction to urge said latch engagement member to move to said lock position and said actuator member being movable in a direction opposite to said one direction to urge said latch engagement to move to said unlock position.

6. The shuttle adapter device as claimed in claim 5, wherein said actuator member is in the form of a tab depending from the base portion of said carrier housing for engagement with a force transmitter.

7. The shuttle adapter device as claimed in claim 1, wherein said latch device includes an actuator member for effecting movement of said latch device from the lock position to the unlock position.

8. The shuttle adapter device as claimed in claim 1, wherein said outside male surface and said inside female surface are formed with at least one key component for complementary engagement with a corresponding key component on an article that can be carried by said carrier housing to ensure a predetermined orientation of the carried article.

9. The shuttle adapter device as claimed in claim 1, wherein the inside female surface and the outside male surface are sized to permit force-free engagement of an article that can be carried on said carrier housing when said latch device is in said unlock position.

10. A shuttle adapter comprising
    a) a carrier housing having a peripheral wall defining an inside female surface and an outside male surface for carrying complementary shaped male or female articles,
    b) a latch device having lock and unlock positions, said latch device being secured to said carrier housing for movement in opposite directions relative to said carrier housing from a first limit position corresponding to the lock position wherein said latch device can interlock with a latch component on a male or female article carried by said carrier housing, to a second limit position corresponding to the unlock position wherein the latch device can be free from engagement with a latch component on a male or female article carried by said carrier housing.

11. The shuttle adapter as claimed in claim 10, wherein said latch device has a latch engagement member that extends into a space defined by the inside female surface.

* * * * *